United States Patent
Liu et al.

(10) Patent No.: US 12,431,227 B2
(45) Date of Patent: Sep. 30, 2025

(54) METHOD AND SYSTEM FOR PROVIDING A PERSONALIZED CANNABINOID TREATMENT REGIMEN

(71) Applicant: GREENWAY DNA INC., Portland, OR (US)

(72) Inventors: Xing-liang Liu, Lake Oswego, OR (US); Douglas Ry Wagner, Pleasant Hill, OR (US); John M. Eustermann, Eagle, ID (US); Gregg M. Steinberg, Fort Collins, CO (US)

(73) Assignee: GREENWAY DNA INC., Fort Collins, CO (US)

( * ) Notice: Subject to any disclaimer, the term of this patent is extended or adjusted under 35 U.S.C. 154(b) by 1189 days.

(21) Appl. No.: 16/729,054

(22) Filed: Dec. 27, 2019

(65) Prior Publication Data

US 2020/0211688 A1 Jul. 2, 2020

Related U.S. Application Data

(60) Provisional application No. 62/786,158, filed on Dec. 28, 2018.

(51) Int. Cl.
| | |
|---|---|
| *G16H 20/10* | (2018.01) |
| *A61K 31/00* | (2006.01) |
| *A61K 31/05* | (2006.01) |
| *A61K 31/352* | (2006.01) |
| *G16B 20/20* | (2019.01) |

(52) U.S. Cl.
CPC ............ *G16H 20/10* (2018.01); *A61K 31/05* (2013.01); *A61K 31/352* (2013.01); *G16B 20/20* (2019.02); *A61K 31/658* (2023.05)

(58) Field of Classification Search
CPC ........ G16B 20/00; G16B 20/20; G16C 20/30; G16H 20/10; G16H 20/90; A61K 31/05; A61K 31/192; A61K 31/352; A61K 31/658

See application file for complete search history.

(56) References Cited

U.S. PATENT DOCUMENTS

| | | |
|---|---|---|
| 2009/0087856 A1 | 4/2009 | Caldwell et al. |
| 2010/0304391 A1 | 12/2010 | Lombard |
| 2011/0189161 A1 | 8/2011 | Blum et al. |
| 2014/0274764 A1 | 9/2014 | Zhu et al. |
| 2017/0061073 A1* | 3/2017 | Sadhasivam ......... C12Q 1/6883 |
| 2021/0172016 A1* | 6/2021 | Fefekos ............... C12Q 1/6883 |

OTHER PUBLICATIONS

Carter et al., Medicinal cannabis: Rational guidelines for dosing, May 2004, IDrugs 7(5): 464-470 (Year: 2004).*

(Continued)

*Primary Examiner* — Jesse P Frumkin
*Assistant Examiner* — Theodore Charles Striegel
(74) *Attorney, Agent, or Firm* — Dorsey & Whitney LLP

(57) ABSTRACT

Methods and systems for providing a personalized cannabinoid treatment regimen to a patient include obtaining genotypes of single nucleotide polymorphisms (SNPs) from a patient's genetic test and modifying base values, such as base dosages or base ratios, using weighting values reflecting the obtained genotypes to obtain regimen values for treating the patient. The regimen values take into account expected responses to cannabinoids based on patient genetic information.

16 Claims, 6 Drawing Sheets

Specification includes a Sequence Listing.

(56) References Cited

OTHER PUBLICATIONS

Lichtman et al., Mice lacking fatty acid amide hydrolase exhibit a cannabinoid receptor-mediated phenotypic hypoalgesia, 2004, Pain 109: 319-327 (Year: 2004).*
Foyzun, Signalling at $CB_2$ receptor and naturally occurring $CB_2$ SNPs variants [Master's Thesis], Dec. 2020, Macquarie University (Year: 2020).*
Yao et al., Adenosine A2a blockade prevents synergy between mu-opiate and cannabinoid CB1 receptors and eliminates heroin-seeking behavior in addicted rats, May 2006, PNAS 103(20): 7877-7882 (Year: 2006).*
Onaivi, Endocannabinoid System, Pharmacogenomics and Response to Therapy, Pharmacogenomics 11(7): 907-910, 2010 (Year: 2010).*
Deuschle Ml, Schredl M, Schilling C, Wüst S, Frank J, Witt SH, Rietschel M, Buckert M, Meyer-Lindenberg A, Schulze TG. Association between a serotonin transporter length polymorphism and primary insomnia. Sleep. Mar. 2010;33(3):343-7.
Smith DR, Stanley CM, Foss T, Boles RG, McKernan K. Rare genetic variants in the endocannabinoid system genes CNR1 and DAGLA are associated with neurological phenotypes in humans. PLoS One. Nov. 16, 2017;12(11):e0187926. doi: 10.1371/journal.pone.0187926. eCollection 2017.
Shi YY, He L. SHEsis, a powerful software platform for analyses of linkage disequilibrium, haplotype construction, and genetic association at polymorphism loci. Cell Res. Feb. 2005;15(2):97-8.
Agrawal A, Edenberg HJ, Foroud T, Bierut LJ, Dunne G, Hinrichs AL, Nurnberger JI, Crowe R, Kuperman S, Schuckit MA, Begleiter H, Porjesz B, Dick DM. Association of GABRA2 with drug dependence in the collaborative study of the genetics of alcoholism sample. Behav Genet. 2006; 36:640-50.
Albert PR. Transcriptional regulation of the 5-HT1A receptor: implications for mental illness. Philos Trans R Soc Lond B Biol Sci. Sep. 5, 2012;367(1601):2402-15. doi: 10.1098/rstb.2011.0376.
Baune BT, Hohoff C, Roehrs T, Deckert J, Arolt V, Domschke K. Serotonin receptor 1A-1019C/G variant: impact on antidepressant pharmacoresponse in melancholic depression? Neurosci Lett. May 9, 2008;436(2):111-5. doi: 10.1016/j.neulet.2008.03.001. Epub Mar. 6, 2008. PMID: 18387740.
Benyamina A, Bonhomme-Faivre L, Picard V, Sabbagh A, Richard D, Blecha L, Rahioui H, Karila L, Lukasiewicz M, Farinotti R, Picard V, Marill C, Reynaud M. Association between ABCB1 C3435T polymorphism and increased risk of cannabis dependence. Prog Neuropsychopharmacol Biol Psychiatry. 2009;33:1270-4.
Bhattacharyya S, Iyegbe C, Atakan Z, Martin-Santos R, Crippa JA, Xu X, Williams S, Brammer M, Rubia K, Prata D, Collier DA, McGuire PK. Protein kinase B (AKT1) genotype mediates sensitivity to cannabis-induced impairments in psychomotor control. Psychol Med. Nov. 2014;44(15):3315-28.
Binder A, May D, Baron R, Maier C, Tölle TR, Treede RD, Berthele A, Faltraco F, Flor H, Gierthmühlen J, Haenisch S, Huge V, Magerl W, Maihöfner C, Richter H, Rolke R, Scherens A, Uçeyler N, Ufer M, Wasner G, Zhu J, Cascorbi I. Transient receptor potential channel polymorphisms are associated with the somatosensory function in neuropathic pain patients. PLoS One. Mar. 29, 2011;6(3):e17387. doi: 10.1371/journal.pone.0017387. PMID: 21468319.
Buttari F, Zagaglia S, Marciano L, Albanese M, Landi D, Nicoletti CG, Mercuri NB, Silvestrini M, Provinciali L, Marfia GA, Mori F, Centonze D. TRPV1 polymorphisms and risk of interferon $î^2$-induced flu-like syndrome in patients with relapsing-remitting multiple sclerosis. J Neuroimmunol. Apr. 15, 2017;305:172-174.
Carey CE, Agrawal A, Zhang B, Conley ED, Degenhardt L, Heath AC, Li D, Lynskey MT, Martin NG, Montgomery GW, Wang T, Bierut LJ, Hariri AR, Nelson EC, Bogdan R. Monoacylglycerol lipase (MGLL) polymorphism rs604300 interacts with childhood adversity to predict cannabis dependence symptoms and amygdala habituation: Evidence from an endocannabinoid system-level analysis. J Abnorm Psychol. Nov. 2015;124(4):860-77.

Carrasquer A, Nebane NM, Williams WM, Song ZH. Functional consequences of nonsynonymous single nucleotide polymorphisms in the CB2 cannabinoid receptor. Pharmacogenet Genom. 2010;20:157-66.
Chen, R., Zhang, J., Fan, N., Teng, Z. Q., Wu, Y., Yang, H., et al. (2013). Delta9-THC-caused synaptic and memory impairments are mediated through COX-2 signaling. Cell, 155, 1154e1165.
Chou WY, Wang CH, Liu PH, Liu CC, Tseng CC, Jawan B. Human opioid receptor A118G polymorphism affects intravenous patient-controlled analgesia morphine consumption after total abdominal hysterectomy. Anesthesiology 2006;105:334-7.
Eum S, Lee AM, Bishop JR. Pharmacogenetic tests for antipsychotic medications: clinical implications and considerations. Dialogues Clin Neurosci. Sep. 2016;18(3):323-337. Review. PMID: 27757066.
Fabbri C, Porcelli S, Serretti A. From pharmacogenetics to pharmacogenomics: the way toward the personalization of antidepressant treatment. Can J Psychiatry. Feb. 2014;59(2):62-75. Review. PMID: 24881125.
Forstenpointner J, Forster M, May D, Hofschulte F, Cascorbi I, Wasner G, Gierthmuhlen J, Baron R. Short Report: TRPV1-polymorphism 1911 A>G alters capsaicin-induced sensory changes in healthy subjects. PLoS One. Aug. 17, 2017;12(8):e0183322. doi: 10.1371/journal.pone.0183322. eCollection 2017.
Furuta T, Ohashi K, Kamata T, Takashima M, Kosuge K, Kawasaki T, Hanai H, Kubota T, Ishizaki T, Kaneko E. Effect of genetic differences in omeprazole metabolism on cure rates for Helicobacter pylori infection and peptic ulcer. Ann Intern Med. Dec. 15, 1998;129(12):1027-30.
Galecki P, Florkowski A, Bieńkiewicz M, Szemraj J. Functional polymorphism of cyclooxygenase-2 gene (G-765C) in depressive patients. Neuropsychobiology. 62(2), 116-120 (2010).
Gong XD, Wang JY, Liu F, Yuan HH, Zhang WY, Guo YH, Jiang B. Gene polymorphisms of OPRM1 A118G and ABCB1 C3435T may influence opioid requirements in Chinese patients with cancer pain. Asian Pac J Cancer Prev. 2013;14(5):2937-43. PMID: 23803057.
Hammerschlag AR, Stringer S, de Leeuw CA, Sniekers S, Taskesen E, Watanabe K, Blanken TF, Dekker K, Te Lindert BHW, Wassing R, Jonsdottir I, Thorleifsson G, Stefansson H, Gislason T, Berger K, Schormair B, Wellmann J, Winkelmann J, Stefansson K, Oexle K, Van Someren EJW, Posthuma D. Genome-wide association analysis of insomnia complaints identifies risk genes and genetic overlap with psychiatric and metabolic traits. Nat Genet. Nov. 2017;49(11):1584-1592. doi: 10.1038/ng.3888. Epub Jun. 12, 2017. PMID: 28604731.
Han S, Yang BZ, Kranzler HR, Oslin D, Anton R, Farrer LA, Gelernter J. Linkage analysis followed by association show NRG1 associated with cannabis dependence in African Americans. Biol Psychiatry. 2012;72:637-44.
Ho BC, Wassink TH, Ziebell S, Andreasen NC. Cannabinoid receptor 1 gene polymorphisms and marijuana misuse interactions on white matter and cognitive deficits in schizophrenia. Schizophrenia Research. 2011; 128:66-75. [PubMed: 21420833].
Holst SC, Valomon A, Landolt HP. Sleep Pharmacogenetics: Personalized Sleep-Wake Therapy. Annu Rev Pharmacol Toxicol. 2016; 56:577-603. doi: 10.1146/annurev-pharmtox-010715-103801. Epub Nov. 2, 2015.
Hopfer CJ, Young SE, Purcell S, Crowley TJ, Stallings MC, Corley RP, Rhee SH, Smolen A, Krauter K, Hewitt JK, Ehringer MA. Cannabis receptor haplotype associated with fewer cannabis dependence symptoms in adolescents. Am J Med Genet B Neuropsychiatr Genet. 2006;141B:895-901.
Howlett AC, Abood ME. CB1 and CB2 Receptor Pharmacology. Adv Pharmacol. 2017;80:169-206. doi: 10.1016/bs.apha.2017.03.007.
Hryhorowicz S, Walczak M, Zakerska-Banaszak O, Słomski R, Skrzypczak-Zielińska M. Pharmacogenetics of Cannabinoids. Eur J Drug Metab Pharmacokinet. Feb. 2018;43(1):1-12. doi: 10.1007/s13318-017-0416-z. Review.
Ishiguro H, Onaivi ES, Horiuchi Y, Imai K, Komaki G, Ishikawa T, Suzuki M, Watanabe Y, Ando T, Higuchi S, Arinami T. Functional polymorphism in the GPR55 gene is associated with anorexia nervosa. Synapse. Feb. 2011;65(2):103-8. doi: 10.1002/syn.20821.
Kebir O, Lafaye G, Blecha L, Chaumette B, Mouaffak F, Laqueille X, Benyamina A. ABCB1 C3435T polymorphism is associated with

(56) References Cited

OTHER PUBLICATIONS tetrahydrocannabinol blood levels in heavy cannabis users. Psychiatry Res. Apr. 2018;262:357-358. doi: 10.1016/j.psychres.2017. 09.006. Epub Sep. 9, 2017.
Ketcherside A, Noble LJ, McIntyre CK, Filbey FM. Cannabinoid Receptor 1 Gene by Cannabis Use Interaction on CB1 Receptor Density. Cannabis Cannabinoid Res. Aug. 1, 2017;2(1):202-209.
Kim H, Mittal DP, Iadarola MJ, Dionne RA (2006). Genetic predictors for acute experimental cold and heat pain sensitivity in humans. J Med Genet 43: e40.
Ko TM, Wong CS, Wu JY, Chen YT. Pharmacogenomics for personalized pain medicine. Acta Anaesthesiol Taiwan. Mar. 2016;54(1):24-30. doi: 10.1016/j.aat.2016.02.001. Epub Mar. 11, 2016. Review. PMID: 26976339.
Lazary J, Lazary A, Gonda X, Benko A, Molnar E, Hunyady L, Juhasz G, Bagdy G. Promoter variants of the cannabinoid receptor 1 gene (CNR1) in interaction with 5-HTTLPR affect the anxious phenotype. Am J Med Genet B Neuropsychiatr Genet, 2009; 150B: 1118-1127.
Lötsch J, Geisslinger G. Pharmacogenetics of new analgesics. Br J Pharmacol. Jun. 2011;163(3):447-60. doi: 10.1111/i.1476-5381.2010. 01074.x. Review.
Maple KE, McDaniel KA, Shollenbarger SG, Lisdahl KM. Dose-dependent cannabis use, depressive symptoms, and FAAH genotype predict sleep quality in emerging adults: a pilot study. Am J Drug Alcohol Abuse. Jul. 2016;42(4):431-40. doi: 10.3109/00952990. 2016.1141913.
McMahon FJ, Buervenich S, Charney D, Lipsky R, Rush AJ, Wilson AF, Sorant AJM, Papanicolaou GJ, Laje G, Fava M, Trivedi MH, Wisniewski SR, Manji H. Variation in the gene encoding the serotonin 2A receptor is associated with outcome of antidepressant treatment. Am J Hum Genet. May 2006;78(5):804-814. doi: 10.1086/ 503820. Epub Mar. 20, 2006.
Mitjans M, Serretti A, Fabbri C et al. Screening genetic variability at the CNR1 gene in both major depression etiology and clinical response to citalopram treatment. Psychopharmacology (Berl.) 227(3), 509-519 (2013).
Onwuameze OE, Nam KW, Epping EA, Wassink TH, Ziebell S, Andreasen NC, Ho Bc. MAPK14 and CNR1 gene variant interactions: effects on brain volume deficits in schizophrenia patients with marijuana misuse. Psychol Med. 2013;43:619-31.
Peiró AM, Planelles B, Juhasz G, Bagdy G, Libert F, Eschalier A, Busserolles J, Sperlagh B, Llerena A. Pharmacogenomics in pain treatment. Drug Metab Pers Ther. Sep. 1, 2016;31(3):131-42. doi: 10.1515/dmpt-2016-0005.
Sagnelli C, Uberti-Foppa C, Hasson H, Bellini G, Minichini C, Salpietro S, et al. (2017) Cannabinoid receptor 2-63 RR variant is independently associated with severe necroinflammation in HIV/ HCVcoinfected patients. PLoS ONE 12(7):e0181890. https://doi. org/10.1371/journal.pone.0181890.
Schroeder F, McIntosh AL, Martin GG, Huang H, Landrock D, Chung S, Landrock KK, Dangott LJ, Li S, Kaczocha M, Murphy EJ, Atshaves BP, Kier AB. Fatty Acid Binding Protein-1 (FABP1) and the Human FABP1 T94A Variant: Roles in the Endocannabinoid System and Dyslipidemias. Lipids. Jun. 2016;51(6):655-76.
Sipe JC, Chiang K, Gerber AL, Beutler E, Cravatt BF. A missense mutation in human fatty acid amide hydrolase associated with problem drug use. Proc Natl Acad Sci USA. 2002;99: 8394-9.
Stout SM, Cimino NM. Exogenous cannabinoids as substrates, inhibitors, and inducers of human drug metabolizing enzymes: a systematic review. Drug Metab Rev. Feb. 2014;46(1):86-95. doi: 10.3109/03602532.2013.849268. Epub Oct. 25, 2013. Review. PMID: 24160757.
Tahamtan A, Samieipoor Y, Nayeri FS, Rahbarimanesh AA, Izadi A, Rashidi-Nezhad A, Tavakoli-Yaraki M, Farahmand M, Bont L, Shokri F, Mokhatri-Azad T, Salimi V. Effects of cannabinoid receptor type 2 in respiratory syncytial virus infection in human subjects and mice. Virulence. Oct. 9, 2017;0. doi: 10.1080/21505594. 2017.1389369.
Uhr M, Tontsch A, Namendorf C, et al. Polymorphisms in the drug transporter gene ABCB1 predict antidepressant treatment response in depression. Neuron. 2008;57(2):203-209.
Woo JH, Kim H, Kim JH, Kim JG. Cannabinoid receptor gene polymorphisms and bone mineral density in Korean postmenopausal women. Menopause. May 2015;22(5):512-9. doi: 10.1097/ GME.0000000000000339.
Zajkowska ZE, Englund A, Zunszain PA. Towards a personalized treatment in depression: endocannabinoids, inflammation and stress response. Pharmacogenomics. Apr. 2014;15(5):687-98.
Zhang PW, Ishiguro H, Ohtsuki T, Hess J, Carillo F, Walther D, Onaivi ES, Arinami T, Uhl GR. Human cannabinoid receptor 1: 5' exons, candidate regulatory regions, polymorphisms, haplotypes and association with polysubstance abuse. Mol Psychiatry. 2004; 9(10):916-931. [PubMed: 15289816].
Haughey HM1, Marshall E, Schacht JP, Louis A, Hutchison KE. Marijuana withdrawal and craving: influence of the cannabinoid receptor 1 (CNR1) and fatty acid amide hydrolase (FAAH) genes. Addiction. Oct. 2008;103(10):1678-86. doi: 10.1111/j.1360-0443. 2008.02292.x. Epub Aug. 14, 2008.
Dobrinas M, Crettol S, Oneda B, Lahyani R, Rotger M, Choong E, Lubomirov R, Csajka C, Eap CB. Contribution of CYP2B6 alleles in explaining extreme (S)-methadone plasma levels: a CYP2B6 gene resequencing study. Pharmacogenet Genomics. Feb. 2013;23(2):84-93. doi: 10.1097/FPC.0b013e32835cb2e2. PMID: 23249875.
Pardini M1, Krueger F, Koenigs M, Raymont V, Hodgkinson C, Zoubak S, Goldman D, Grafman J. Fatty-acid amide hydrolase polymorphisms and post-traumatic stress disorder after penetrating brain injury. Transl Psychiatry. Jan. 31, 2012;2:e75. doi: 10.1038/ tp.2012.1.
Horstmann S1, Lucae S, Menke A, Hennings JM, Ising M, Roeske D, Müller-Myhsok B, Holsboer F, Binder EB. Polymorphisms in GRIK4, HTR2A, and FKBP5 show interactive effects in predicting remission to antidepressant treatment. Neuropsychopharmacology. Feb. 2010;35(3):727-40. doi: 10.1038/npp.2009.180. Epub Nov. 18, 2009.

\* cited by examiner

METHOD AND SYSTEM FOR PROVIDING A PERSONALIZED CANNABINOID TREATMENT REGIMEN

CROSS-REFERENCE TO RELATED APPLICATIONS

This application claims the benefit of U.S. Provisional Patent Application Ser. No. 62/786,158, filed Dec. 28, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 23, 2019, is named GDNA-1-1001_SL.txt and is 17,458 bytes in size.

FIELD

The present invention is directed to the area of methods and systems for determining and providing treatment parameters for use of cannabinoids. The present invention is also directed to methods and systems for utilizing patient DNA information to provide personalized cannabinoid treatment regimen.

BACKGROUND

Over 100 chemically and biosynthetically related cannabinoids, and well over 100 terpenes, have been identified in *Cannabis* to date. Many of the compounds have been shown to have therapeutic or health-related benefits.

There are two major cannabinoids, cannabidiol (CBD) and 49-tetrahydrocannabinol (THC), along with several other less potent cannabinoids, such as cannabichromene (CBC), cannabichromevarin (CBCV), $\Delta^9$-tetrahydrocannabivarin (THCV), cannabigerol (CBG), cannabigerovarin (CBGV), cannabidivarin (CBDV), and cannabinol (CBN).

THC shows wide clinical benefit for symptoms of diseases such as energy metabolism, pain and inflammation, neuroprotection, Alzheimer's disease, Huntington's disease, anxiety and fear, sleep disorders, emesis, gastrointestinal disorders, cardiovascular disorders, cancer, and so on. A synthetic analog of THC, nabilone, was approved for the suppression of the nausea and vomiting caused by chemotherapy.

CBD is anxiolytic, antidepressant, antipsychotic, anticonvulsant, antinausea, antioxidant, anti-inflammatory, antiarthritic, and antineoplastic. Within the central nervous system (CNS) it is effective in animal models of epilepsy, anxiety, psychosis, and diseases of the basal ganglia, such as Parkinson's and Huntington's diseases, and CBD also shows beneficial effects in treatments of psychosis, epilepsy, anxiety, sleep, neuroprotection and neurodegenerative diseases, such as, Alzheimer's disease, Parkinson's disease, and Huntington's disease, pain, inflammation, autoimmunity, and retinal diseases, emesis, cancer, and so on.

Of the less potent cannabinoids there are many investigations which demonstrate that at least some of the therapeutic benefits of THC and CBD are also available from a handful of other cannabinoids, such as, CBC, CBG, CBDV, THCV, $\Delta^9$-tetrahydrocannabinolic acid (THCA), and cannabidiolic acid (CBDA). For example, the US National Academy of Sciences, Engineering and Medicine (NASEM) reported clinical evidence of an effect on chronic pain and good evidence of an effect on anxiety and sleep disturbance (i.e. insomnia).

BRIEF SUMMARY

One embodiment is a method of providing a personalized cannabinoid treatment regimen to a patient. The method includes obtaining two or more base values, wherein each of the base values is a different one of the following: a) a base dosage for a first cannabinoid; b) a base dosage for a second cannabinoid; c) a base dosage for a combination of the first and second cannabinoids; or d) a base ratio of the first and second cannabinoids; for each of a plurality of single nucleotide polymorphisms (SNPs) in a selected set of SNPs, obtaining, from a genetic test of the patient, a genotype for the SNP; for each of the SNPs in the selected set of SNPs, obtaining, for the obtained genotype of the SNP, at least one weighting value which reflects, for the obtained genotype of the SNP, one or more responses selected from the following: i) a response to the first and second cannabinoids; ii) a response to the first cannabinoid only; iii) a response to the second cannabinoid only; or iv) cannabinoid dependency; modifying the two or more base values based on the obtained weighting values to produce two or more regimen values, wherein each of the regimen values is a different one of the following: a) a regimen dosage for the first cannabinoid; b) a regimen dosage for the second cannabinoid; c) a regimen dosage for a combination of the first and second cannabinoids; or d) a regimen ratio of the first and second cannabinoids; and treating the patient using the first and second cannabinoids according to the two or more regimen values.

In at least some embodiments, the first cannabinoid is cannabidiol (CBD) and the second cannabinoid is $\Delta^9$-tetrahydrocannabinol (THC). In at least some embodiments, the method further includes obtaining a condition for treatment, wherein the selected set of SNPs includes a plurality of SNPs associated with the condition. In at least some embodiments, a value of at least one of the base values is dependent on the condition. In at least some embodiments, the condition is selected from pain, depression, anxiety, fear, sleep disorder, insomnia, energy metabolism disorder, inflammation, neuroprotection. Alzheimer's disease, Huntington's disease, Parkinson's disease, emesis, gastrointestinal disorder, cardiovascular disorder, cancer, nausea, vomiting, epilepsy, psychosis, diseases of the basal ganglia, neurodegenerative diseases, autoimmune disorder, retinal diseases, arthritis, convulsions, neoplastic diseases, or any combination thereof.

In at least some embodiments, modifying the two or more base values includes modifying at least one of the base values by multiplying the at least one of the base values by a product of at least one of the weighting values for each of a plurality of the SNPs.

In at least some embodiments, obtaining at least one weighting value includes obtaining the weighting values for each of the following responses individually: i) the response to the first and second cannabinoids, ii) the response to the first cannabinoid only; iii) the response to the second cannabinoid only, or iv) the cannabinoid dependency. In at least some embodiments, modifying the two or more base values includes modifying at least one first value, selected from the two or more base values, using the weighting values for a first one of the responses to produce at least one first intermediate value; modifying at least one second value, selected from the two or more base values and the at least one first intermediate value, using the weighting values for a second one of the responses to produce at least one second intermediate value; modifying at least one third value, selected from the two or more base values, the at least one first intermediate value, and the at least one second intermediate value, using the weighting values for a third one of the responses to produce at least one third intermediate value; and modifying at least one fourth value, selected from the two or more base values, the at least one first intermediate value, the at least one second intermediate value, and the at least one third intermediate value, using the weighting values for a fourth one of the responses to produce at least one of the regimen values.

In at least some embodiments, obtaining the two or base values includes determining the two or more base values using at least one factor selected from patient weight, condition for treatment, patient age, patient gender, patient body type, other medications taken by patient, or results of a patient blood test.

Another embodiment is a system for providing an individualized cannabinoid treatment regimen. The system includes a processor configured to perform actions to produce the individualized cannabinoid treatment regimen, the actions including: obtaining two or more base values, wherein each of the base values is a different one of the following: a) a base dosage for a first cannabinoid; b) a base dosage for a second cannabinoid; c) a base dosage for a combination of the first and second cannabinoids; or d) a base ratio of the first and second cannabinoids; for each of a plurality of single nucleotide polymorphisms (SNPs) in a selected set of SNPs, obtaining, from a genetic test of the patient, a genotype for the SNP; for each of the SNPs in the selected set of SNPs, obtaining, for the obtained genotype of the SNP, at least one weighting value which reflects, for the obtained genotype of the SNP, one or more responses selected from the following: i) a response to the first and second cannabinoids; ii) a response to the first cannabinoid only; iii) a response to the second cannabinoid only; or iv) cannabinoid dependency; and modifying the two or more base values based on the obtained weighting values to produce two or more regimen values, wherein each of the regimen values is a different one of the following: a) a regimen dosage for the first cannabinoid; b) a regimen dosage for the second cannabinoid; c) a regimen dosage for a combination of the first and second cannabinoids; or d) a regimen ratio of the first and second cannabinoids.

In at least some embodiments, the first cannabinoid is cannabidiol (CBD) and the second cannabinoid is $\Delta^9$-tetrahydrocannabinol (THC). In at least some embodiments, the actions further include obtaining a condition for treatment, wherein the selected set of SNPs includes a plurality of SNPs associated with the condition. In at least some embodiments, modifying the two or more base values includes modifying at least one of the base values by multiplying the at least one of the base values by a product of at least one of the weighting values for each of a plurality of the SNPs.

In at least some embodiments, obtaining at least one weighting value includes obtaining the weighting values for each of the following responses individually: i) the response to the first and second cannabinoids, ii) the response to the first cannabinoid only; iii) the response to the second cannabinoid only, or iv) the cannabinoid dependency. In at least some embodiments, modifying the two or more base values includes modifying at least one first value, selected from the two or more base values, using the weighting values for a first one of the responses to produce at least one first intermediate value; modifying at least one second value, selected from the two or more base values and the at least one first intermediate value, using the weighting values for a second one of the responses to produce at least one second intermediate value; modifying at least one third value, selected from the two or more base values, the at least one first intermediate value, and the at least one second intermediate value, using the weighting values for a third one of the responses to produce at least one third intermediate value; and modifying at least one fourth value, selected from the two or more base values, the at least one first intermediate value, the at least one second intermediate value, and the at least one third intermediate value, using the weighting values for a fourth one of the responses to produce at least one of the regimen values.

Another embodiment is a non-transitory processor readable storage media that includes instructions for producing an individualized cannabinoid treatment regimen, wherein execution of the instructions by one or more processors cause the one or more processors to perform actions, including: obtaining two or more base values, wherein each of the base values is a different one of the following: a) a base dosage for a first cannabinoid; b) a base dosage for a second cannabinoid; c) a base dosage for a combination of the first and second cannabinoids; or d) a base ratio of the first and second cannabinoids; for each of a plurality of single nucleotide polymorphisms (SNPs) in a selected set of SNPs, obtaining, from a genetic test of the patient, a genotype for the SNP; for each of the SNPs in the selected set of SNPs, obtaining, for the obtained genotype of the SNP, at least one weighting value which reflects, for the obtained genotype of the SNP, one or more responses selected from the following: i) a response to the first and second cannabinoids; ii) a response to the first cannabinoid only; iii) a response to the second cannabinoid only; or iv) cannabinoid dependency; and modifying the two or more base values based on the obtained weighting values to produce two or more regimen values, wherein each of the regimen values is a different one of the following: a) a regimen dosage for the first cannabinoid; b) a regimen dosage for the second cannabinoid; c) a regimen dosage for a combination of the first and second cannabinoids; or d) a regimen ratio of the first and second cannabinoids.

In at least some embodiments, the first cannabinoid is cannabidiol (CBD) and the second cannabinoid is $\Delta^9$-tetrahydrocannabinol (THC). In at least some embodiments, the actions further include obtaining a condition for treatment, wherein the selected set of SNPs includes a plurality of SNPs associated with the condition.

In at least some embodiments, obtaining at least one weighting value includes obtaining the weighting values for each of the following responses individually: i) the response to the first and second cannabinoids, ii) the response to the first cannabinoid only; iii) the response to the second cannabinoid only, or iv) the cannabinoid dependency. In at least some embodiments, modifying the two or more base values includes modifying at least one first value, selected from the two or more base values, using the weighting values for a first one of the responses to produce at least one first intermediate value; modifying at least one second value, selected from the two or more base values and the at least one first intermediate value, using the weighting values for a second one of the responses to produce at least one second intermediate value; modifying at least one third value, selected from the two or more base values, the at least one first intermediate value, and the at least one second intermediate value, using the weighting values for a third one of the responses to produce at least one third intermediate value; and modifying at least one fourth value, selected from the two or more base values, the at least one first intermediate value, the at least one second intermediate value, and the at least one third intermediate value, using the weighting values for a fourth one of the responses to produce at least one of the regimen values.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of methods and systems for determining and providing treatment parameters for use of cannabinoids. The present invention is also directed to methods and systems for utilizing patient DNA information to provide personalized cannabinoid treatment regimen.

Figure 1:
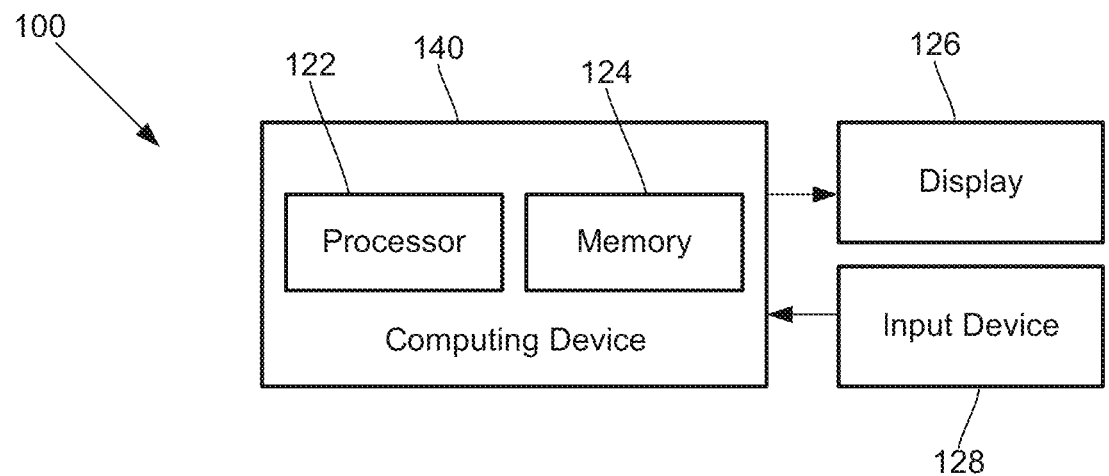
FIG. 1 is a block diagram of one embodiment of a computing system for practicing the invention.

In at least some embodiments, the systems and methods described herein can utilize a computer system for determining recommended regimen values for treatment using two or more cannabinoids. FIG. 1 is a block diagram of components of one embodiment of such a computer system 100. The computer system 100 can include a computing device 120 or any other similar device that includes a processor 122 and a memory 124, a display 126, and an input device 128.

The computing device 120 can be a computer, tablet, mobile device, field programmable gate array (FPGA), or any other suitable device for processing information. The computing device 120 can be local to the user (such as a clinician or patient) or can include components that are non-local to the user including one or both of the processor 122 or memory 124 (or portions thereof). For example, in at least some embodiments, the user may operate a terminal that is connected to a non-local computing device. In other embodiments, the memory 124 can be non-local to the user.

The computing device 120 can utilize any suitable processor 122 including one or more hardware processors that may be local to the user or non-local to the user or other components of the computing device. The processor 122 is configured to execute instructions provided to the processor 122.

Any suitable memory 124 can be used for the computing device 120. The memory 124 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 126 can be any suitable display device, such as a monitor, screen, or the like, and can include a printer. In some embodiments, the display is optional. In some embodiments, the display 126 may be integrated into a single unit with the computing device 120, such as a tablet, smart phone, or smart watch. In at least some embodiments, the display is not local to the user. The input device 128 can be, for example, a keyboard, mouse, touch screen, track ball, joystick, voice recognition system, or any combination thereof, or the like. In at least some embodiments, the input device is not local to the user.

In at least some embodiments, the systems and methods described herein can provide personalized information, such as personalized treatment regimen values including personalized dosages, that can facilitate, or even accelerate, an individual's treatment or path to wellness using cannabinoids, the medicinal compounds produced from *Cannabis* and hemp. In at least some embodiments, the systems and methods utilize personal genetic information to estimate how an individual's endocannabinoid system may be predisposed to function in response to cannabinoids. This information can facilitate a better understanding of the potential efficacy of cannabinoid dose regimes for the relief of conditions including, but not limited to, pain, depression, anxiety, fear, sleep disorder, insomnia, energy metabolism disorder, inflammation, neuroprotection, Alzheimer's disease, Huntington's disease, Parkinson's disease, emesis, gastrointestinal disorder, cardiovascular disorder, cancer, nausea, vomiting, epilepsy, psychosis, diseases of the basal ganglia, neurodegenerative diseases, autoimmune disorder, retinal diseases, arthritis, convulsions, neoplastic diseases, or the like.

The human endocannabinoid system includes receptors, enzymes, and proteins that process cannabinoids as well as other compounds that can regulate or otherwise affect aspects of human health and wellbeing. DNA encodes the genetic information to produce these receptors, enzymes, and metabolic proteins and there is substantial variance between individuals with respect to the DNA sequences for these genes. This natural genetic variation can affect how the endocannabinoid system functions in each person. The DNA variation can be determined by DNA sequence analysis to provide an overview of the genetic composition of the genes involved in the perception and response to cannabinoids.

Knowledge of individual endocannabinoid system, based on personal genetic information, can be used to provide insights as to the potential response to particular dose regimes of cannabinoids to treat, for example, conditions such as pain, depression, anxiety, fear, sleep disorder, insomnia, energy metabolism disorder, inflammation, neuroprotection, Alzheimer's disease, Huntington's disease, Parkinson's disease, emesis, gastrointestinal disorder, cardiovascular disorder, cancer, nausea, vomiting, epilepsy, psychosis, diseases of the basal ganglia, neurodegenerative diseases, autoimmune disorder, retinal diseases, arthritis, convulsions, neoplastic diseases, or the like. According to a 2016 WebMD survey, 48% of medical *Cannabis* patients take between 3 to 6 months or longer, and spend up to $3,000, to find the appropriate cannabinoid combination to address their condition. The systems and methods described herein can be used to facilitate efficiently identifying a dosage, and ratio, of CBD and THC or other cannabinoids to treat a desired condition or conditions based on patient genetic information.

Studies of THC lead to the discovery of a cannabinoid receptor, CB1, and the human endocannabinoid system (ECS). In at least some embodiments, the ECS is defined as the ensemble of: a) two 7-transmembrane-domain and G protein-coupled receptors (GPCRs) for THC-cannabinoid receptor type 1 (CB1) and cannabinoid receptor type 2 (CB2); b) two endogenous ligands, the "endocannabinoids" N-arachidonoylethanolamine (anandamide) and 2-arachidonoylglycerol (2-AG); and c) the enzymes responsible for a) endocannabinoid biosynthesis (including N-acyl-phosphatidyl-ethanolamine-selective phospholipase D (NAPE-PLD) and diacylglycerol lipases (DAGL) α and β, for anandamide and 2-AG, respectively) and b) hydrolytic inactivation (including fatty acid amide hydrolase (FAAH) and monoacylglycerol lipase (MAGL), for anandamide and 2-AG, respectively).

Endocannabinoids and the ECS can regulate synaptic plasticity in the central nervous system to modulate brain functions such as memory, mood and emotions, and pain perceptions. The ECS may promote both non-rapid-eye movement and rapid-eye-movement sleep by interacting with melanin-concentrating hormone neurons in the lateral hypothalamus.

THC and THCV bind with high affinity to CB1 and CB2 (with agonist and antagonist activity for THC and THCV, respectively). CBD, on the other hand, may indirectly affect CB1/CB2 by weakly inhibiting AEA enzymatic hydrolysis (for example, inhibiting FAAH) to regulate the ECS and effect the pain, anxiety, and insomnia conditions. Cannabinoids also exhibit moderate activity on a wide array of molecular targets (for example, orphan GPCRs) including several channels belonging to the transient receptor potential (TRP) family, such as rat and human transient receptor potential vanilloid subtype 1 channel (TRPV1), 5-hydroxytryptamine receptors (5-HT) (for example, HT1A or serotonin receptors) to modulate brain functions (for example, pain perceptions).

The therapeutic efficacy of cannabinoids may be impacted by genetic variations of the receptor genes (CB1, CB2, TRPV1, and HT1A), the transport genes (ATP-Binding Cassette Subfamily B member 1 (ABCB1), Solute Carrier Family 6 member 4 (serotonin transporter) (SLC6A4)); the metabolism genes (Cytochrome P450, CYP2C9 and CYP3A4, and Catechol-O-Methyltransferase (COMT)), as well as interactions of the genetic variations between these genes. Pharmacogenomic and pharmacogenetic test-guided target therapy, as described herein, can provide a cost-effective approach to personalized treatments, and is particularly attractive for complex diseases or disorders for which it is often difficult to tailor treatments (for example, pain, depression, anxiety, fear, sleep disorder, insomnia, energy metabolism disorder, inflammation, neuroprotection, Alzheimer's disease, Huntington's disease, Parkinson's disease, emesis, gastrointestinal disorder, cardiovascular disorder, cancer, nausea, vomiting, epilepsy, psychosis, diseases of the basal ganglia, neurodegenerative diseases, autoimmune disorder, retinal diseases, arthritis, convulsions, neoplastic diseases, or the like). Chronic pain, anxiety, depression, and sleep disorders are used herein as examples.

Chronic pain is one example of a malady which may be treated by medical *Cannabis*. There is substantial clinical evidence that *Cannabis* is an effective treatment for chronic pain, often with fewer side effects compared to opioids. It is believed that endocannabinoids localize throughout the brain and activate CB1 and TRPV1. It is believed that stimulation of CB1 can exert anti-inflammatory and analgesic effects, whereas TRPV1 activation may increase inflammation, pain and fever through the enhancement of neurotransmitter release and the secretion of pro-inflammatory cytokines.

Genetic variations of cannabinoid receptors (CB1 and CB2), the principle cannabinoid catabolic enzyme (FAAH), the transport gene (ABCB1), and the metabolism genes (COMT and Cytochrome P450, CYP2C9 and CYP3A4) may result in different gene expression levels or activity in response to cannabinoids, as well as different levels of association to multiple drug dependence and adverse drug reactions (ADRs). For example, variations in TRPV1 have been associated with higher pain tolerance or higher risk of interferon-induced side effects in patients with multiple sclerosis. Genetic variations of the transport gene (ABCB1) and the metabolism genes (COMT and Cytochrome P450, CYP2C9 and CYP3A4) have been associated with drug efficacy and ADRs in pharmacogenomic studies. Identification of these genetic variations in an individual can be used to make recommendations to the individual with respect to the safety and efficacy of personalized *Cannabis* use in pain management or other treatments.

Excessive fear and anxiety are symptoms of a number of neuropsychiatric disorders including generalized anxiety disorder (GAD), panic disorder (PD), and social anxiety disorder (SAD). The endocannabinoid system (ECS) can modulate synaptic plasticity that affect learning and response to emotional salient and aversive events. It is believed that activation of CB1 can produce anxiolytic effects and produce negative feedback to the neuroendocrine stress response. It is believed that chronic stress impairs ECS signaling in the hippocampus and amygdala and can lead to anxiety. It is believed that genetic variants of CB1 and FAAH in ECS are linked to high anxiety, particularly when interacting with gene variations in other systems, such as the serotonin transporter gene (SLC6A4), or with early life stress.

*Cannabis* use demonstrates a level of efficacy for anxiety reduction in studies. Anxiety may also be partially regulated by serotonin levels for which a number of currently available pharmacological treatments were developed, such as selective serotonin reuptake inhibitors (SSRIs), serotonin-norepinephrine reuptake inhibitors, benzodiazepines, monoamine oxidase inhibitors, tricyclic antidepressant (TCA) drugs, and partial 5-HT1A receptor agonists. in particular. Genetic variations in the following genes have been shown to affect therapeutic efficacy and antidepressant (AD) response: SLC6A4, Serotonin Receptor 1A and 2A (HTR1A and HTR2A), Brain Derived Neurotrophic Factor (BDNF), and COMT. By genetic testing of these AD response gene variants along with the generic variants of CB1 and FAAH genes of the ECS and Cytochrome P450 genes that catabolize *Cannabis* and antidepressants, a personalized anxiety/depression treatment recommendation for CBD and THC use can be rendered, as described herein.

Insomnia is a common sleep disorder and while its cause is often unknown it may often be a consequence of a chronic disease associated with stress, pain, or depression. It is believed that administration of cannabinoids can be an effective treatment as THC has been found to promote sleep in both humans and animals. Further, CB1 activation may lead to induction of sleep in a manner blocked by a selective CB1 antagonist. Genetic variants of FAAH were found to be associated with poor sleep quality.

Genetic variants of the B3 subunit of the $GABA_A$ receptor and the serotonin transporter are associated with insomnia. Currently, drug treatments of insomnia include classes of antagonists of histamine HI receptors such as diphenhydramine; low-dose doxepin (a TCA with high affinity for the HI receptor); Mirtazapine (an antidepressant with 5-HT and His antagonistic properties); benzodiazepines (BZD) and non-benzodiazepine agonistic allosteric modulators of $GABA_A$ receptors; and exogenous melatonin. Genetic variants affecting exposure and sensitivity to drugs that improve sleep include the isoenzymes of Cytochrome P450s such as CYP2D6, CYP1A2, CYP2C9, and CYP2C19; the HTR1B and HTR2A genes, and the melatonin receptor genes (MTNR1A). Genome-wide association analysis of insomnia complaints identified one high risk locus-MEIS 1. Personalized insomnia therapy based on CBD and THC use can be recommended by testing these gene variants, as described herein.

Genetic testing can be utilized to investigate single nucleotide polymorphisms (SNPs) of interest in genes associated with the ECS. Tables 1 to 4 provide examples of SNPs of interest relating to *Cannabis* response (Table 1), pain treatment (Table 2), anxiety/depression (Table 3), and sleep disorders/insomnia (Table 4). As an example of the methods and systems, after analyzing the SNPs of interest in genes associated with the ECS, 38 SNPs of high potency, as determined by published studies, were selected and are presented in Tables 5A and 5B. PCR amplification and Next Generation Sequencing (NGS) sequencing primers were designed to investigate these SNPs.

It will be understood, however, that other selections of SNPs can be used. Moreover, SNPs may be selected based on factors such as, the condition being treated, whether cannabinoid dependency is to be investigated, the potency of SNP variation, and the like.

In one example, PCR primers were designed using the Primer3plus platform (available at primer3plus.com/), although any other suitable method of primer design can be used. Examples of primers are presented in Table 5 below. The PCR primers were obtained from Integrated DNA Technologies, Inc. (Skokie, Illinois, United States) after adding proper sequence adaptors for NGS sequencing. In this example, using one control human DNA sample as the template, PCR amplification showed all amplified unique products. In this example, nine PCR products were larger than the expected size, which is not unexpected due to continuous updating of human genome sequencing and SNP annotations.

In this example, the PCR products were sequenced under MiSeq System (Illumina, San Diego, CA, United States) and analyzed. High quality genome sequence coverages (the number of sequence reads per SNP) were produced, and 34 of the SNPs were successfully read through the SNP genome locations with NGS sequence read coverages from 348 to 11,263 as shown in Table 6A. Minor mutation alleles were identified from 18 SNPs as shown in the "Mutation Call: Relative to CDS" column in Table 6B.

Over the 100 chemically and biosynthetically related cannabinoids that have been identified in *Cannabis* to date, the two major components, cannabidiol (CBD) and $\Delta^9$-tetrahydrocannabinol (THC), are widely adopted in the treatment and clinical studies with various dosages and ratios for different conditions. There are many different factors that can play a part in the effectiveness and user experiences of *Cannabis* treatments. These include, but are not limited to, a) the symptoms or conditions to be treated, b) the intensity or progressiveness of the system or condition, c) individual biology and metabolism, d) the individual's endocannabinoid system and how it reacts to CBD and THC, e) body weight, f) individual sensitivity to *Cannabis* compounds, g) other medications being taken, and h) daily food intake patterns including the quantity and quality of the food.

A common conventional practice to determine the dosage and ratio of CBD and THC begins with the lowest dosage and increases the dosage every two to four days based on the effects on the user. This process may take months and cost thousands of dollars before finding an appropriate dosage and ratio for a user's condition, for example, pain, anxiety/depression, insomnia, or the like, as well as the THC dependence of the user.

The methods and systems described herein utilize a pharmacogenomics approach and facilitate estimation of dosage and ratio of CBD and THC for treatment of a condition and, at least in some instances, also account for THC dependence. The systems and methods use genetic variations in the endocannabinoid systems to account for the impact in the responses to CBD and THC or other cannabinoids.

The systems and methods described herein can utilize any combination of the genes and SNPs described above or any other genes and SNPs. The systems and methods utilize a selected set of SNPs that contains multiple SNPs. In some embodiments, the systems and methods may utilize a selected set of SNPs regardless of the condition to be treated. In other embodiments, some or all of the SNPs in the selected set of SNPs may be selected based on the condition to be treated. In at least some embodiments, the number or identity of the SNPs in the selected set of SNPs may be modified by factors such as, for example, the condition to be treated, the results of a genetic test (for example, if the genotype of a SNP is not sufficiently determined), or the like or any combination thereof. As an example, from the 19 genes, 38 SNPs, 108 genotypes of the 38 SNPs, as well as five haplotype SNPs from CNR1, GABRA2, and MAPK14 genes, as presented in Tables 1 to 4, a selection of 38 SNPs is presented in Tables 5A, 5B, and 6. Table 7 also presents the different alleles for each SNP.

Figure 2:
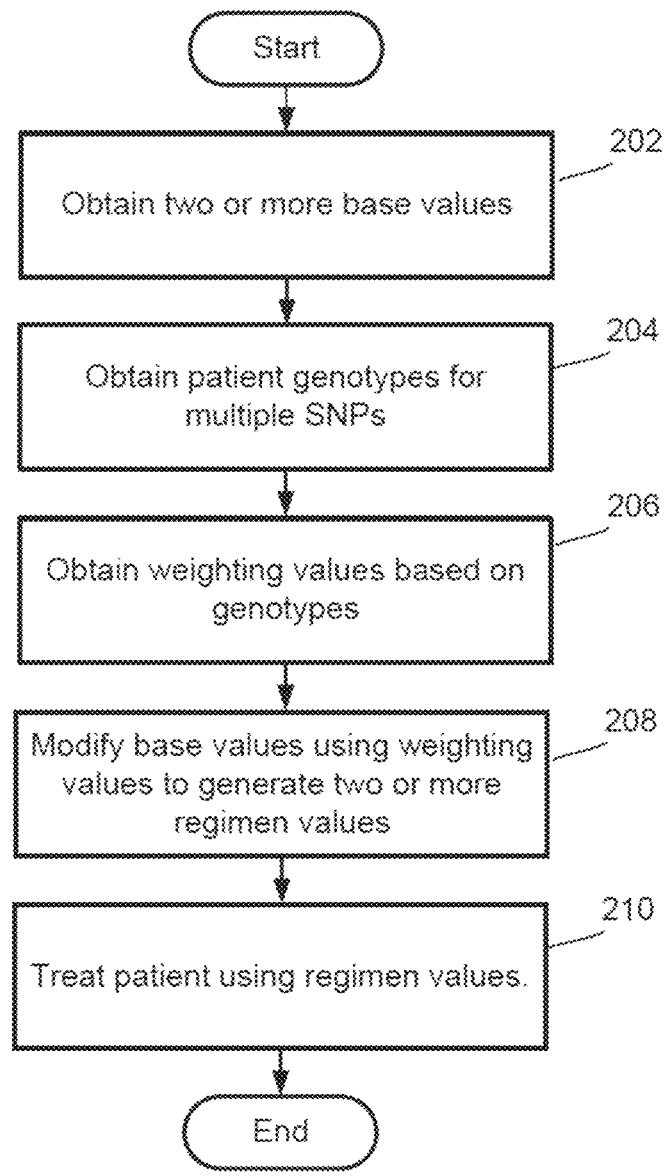
FIG. 2 is a flow chart of one embodiment of a method of producing an individualized cannabinoid treatment regimen, according to the invention.

FIG. 2 is a flow chart for one method of determining regimen values for treating a patient. The methods and systems described herein will describe treatment using two cannabinoids as an example and, in particular, will describe treatment using CBD and THC as an example. It will be understood, however, that the systems and methods described herein can be utilized for determining regimen values, such as dosage or ratio of CBD to THC, and treatments using one, two, three, four, or more cannabinoids and using cannabinoids other than CBD or THC.

In steps 202, two or more base values are obtained. Examples of base values include the following: a) a base dosage for a first cannabinoid, such as CDB, b) a base dosage for a second cannabinoid such as THC, c) a base dosage for a combination of the first and second cannabinoids (for example, CDB and THC), or d) a base ratio of the first and second cannabinoids (for example, CBD/THC). In one embodiments, the method or system uses a starting CBD dosage, a starting THC dosage, and a starting CBD/THC ratio (or any two of these base values).

The base values can be selected using any suitable method including, but not limited to, published recommendations, clinician experience, public research studies, other data, or the like. The base values may take into account one or more factors, such as, but not limited to, condition to be treated, age, body weight, gender, body type, other medications, results of blood tests or other tests, or the like or any combination thereof. As an example, in one embodiment, for starting CBD and THC dosage and CBD/THC ratio, published recommendations in Leinow and Birnbaum. CBD, A Patient's Guide to Medical *Cannabis* (North Atlantic Books, Berkeley, California, 2017—incorporated herein by reference in its entirety) were used as a middle point base dosage (D1—Table 9) and ratio (R1—Table 9) after factoring the medical conditions, age, and body weight of the patient.

In step 204, a genotype for each SNP in a selected set of SNPs is obtained from a genetic test of the patient. As indicated above, the set of SNPs may be any suitable set of SNPs or may include SNPs selected specifically for the condition to be treated. Any suitable method can be used for determining the genotype including, but not limited to, PCR amplification and sequence determination. Table 8 presents one example of a set of SNPs and a corresponding allele, determined from a genetic test, for each of the SNPs.

In step 206, one or more weighting values are obtained based on the genotypes of the SNPs. Each of the weighting values reflects, for the obtained genotype of the SNP associated with the weighting value, one or more responses selected from the following: i) a response to the first and second cannabinoids (for example, CBD and THC); ii) a response to the first cannabinoid only (for example, CBD only); iii) a response to the second cannabinoid only (for example, THC only); or iv) cannabinoid dependency (i.e., a likelihood for developing dependency on a drug such as, for example, THC). Table 8 presents one example different weighting values for the determined allele for each of the SNPs (see columns labeled "*Cannabis* Dosage", CBD Dosage", "THC Dosage" and "Drug Dependence (THC)"). Table 7 presents one example of weighting values for each of the alleles for each SNP (see columns labeled "*Cannabis* Dosage", CBD Dosage", "THC Dosage" and "Drug Dependence (THC)"). In this illustrated embodiment, differences in weighting values were made in 0.25 increments, but it will be understood that other arrangements of weighting values can be determined with different in increments of 0.01, 0.05, 0.10, or the like or any other suitable increment.

In at least some embodiments, the weighting value is in the range of 0 to 5 or more or the range of 0 to 2 or more. In these embodiments, the weighting values may multiple the base value (or an intermediate value) to modify the base value (or intermediate value) as illustrated in the examples below. Thus, a weighting value of 1 indicates that the particular genotype associated with that weighting value is not expected to have an effect on the base value. In contrast, a weighting value of less than 1 for a base value related to dosage may indicate that, for the patient's genotype, the cannabinoid may have larger than average effect, thereby suggesting that a lower dosage is recommended. Similarly, a weighting value of more than 1 for a base value related to dosage may indicate that, for the patient's genotype, the cannabinoid may have smaller than average effect, thereby suggesting that a higher dosage is recommended.

The weighting values also reflect, in part, the use of a product function, as described below. It will be understood that other functions, such as a summation function or an exponential function, may be used which would then incorporate a different range for the weighting values. In some embodiments, the weighting values may also be presented as a percentile or fraction.

The weighting values can be selected based on literature studies, practitioner experience, public research studies, or other data, or the like or any combination thereof. Moreover, the weighting values may also take into account one or more factors, such as, for example, patient weight, patient gender, or the like or any combination thereof.

As an example, in at least some embodiments, the individual weighting values for each of the SNPS are determined using one or both of the following: 1) direct evidence of increasing or decreasing gene activity or treatment response to multiple drugs (for example, in one embodiment, the SNP variants from COMT, CYP2C9, CYP2C19, ABCB1, or HTR2A genes were evaluated based on this evidence) or 2) indirect evidence of increasing or decreasing of gene expressions, which typically leads to increased or reduced activity or responsiveness under cannabinoid treatments (for example, in one embodiment, the SNP variants CNR1, CNR2, HTR1A, HTR2A, AKT1, NRG1, or FAAH genes were evaluated based on this evidence).

In step 208, the weighting values are used to modify the base values in order to generate two or more regimen values. The regimen values can be, for example, a) a regimen dosage for the first cannabinoid (for example, CBD), b) a regimen dosage for the second cannabinoid (for example, THC), c) a regimen dosage for a combination of the first and second cannabinoids (for example, CBD or THC), or d) a regimen ratio of the first and second cannabinoids (for example, CBD/THC). In at least some embodiments, a report is provided to the patient or a clinician with the regimen values. The modification of the base values using the weighting values may include generating intermediate values and may include two or more substeps (examples provided below in the description of the flowcharts of FIGS. 3 and 4).

The modification of the base values, based on the weighting values, personalizes the treatment for the patient based on the patient's genetic information. The weighting values are used to personalize the treatment by accounting for the patient's genotypes in the selected set of SNPs. As an example, as indicated above, in some embodiments, the weighting values range from 0 to 2 or more and are used as a multiplier for the base value (or other intermediate value) to generate the regimen values. A specific example of one embodiment of this modification method is provided below. It will be understood, however, that other calculational methods for modification can be used including, but not limited to, summation of weighting values, averaging of weighting values, or the like. In such cases, the weighting values are likely to be given a different range of possible values.

In step 210, the patient can be treated using the regimen values. As indicated above, the regimen values personalize the treatment. It will be understood, however, that these regimen values may simply be a starting point for the treatment and further modifications may be made over time based, for example, on patient experience with the treatment, worsening or improvement of the condition, changes in medical situation (which may impact overall health), age, weight, or the like or any combination thereof.

One or more weighting values can be associated with the genotype of each SNP. For example, the genotype of each SNP may have a single weighting value associated with that genotype to represent the general response of a patient with that genotype to cannabinoids.

Alternatively, multiple (for example, two, three, four, or more) weighting values can be associated with at least some (or even all) of the SNPs and their genotypes. Such an arrangement can be used to account for different types of impact. For example, different weighting values may be provided for each of the following four different responses (or any subset of these four responses): i) a response to the first and second cannabinoids (for example, CBD and THC); ii) a response to the first cannabinoid only (for example, CBD only); iii) a response to the second cannabinoid only (for example, THC only); or iv) cannabinoid dependency (i.e., a likelihood for developing dependency on a drug such as, for example, THC). In at least some embodiments, a weighting value for each of these responses is provided for each genotype of each SNP. Alternatively, only a subset of the SNPs may be considered for each type or response and, therefore, weighting values for that type or response are provided for only that subset of SNPs.

As an example, in at least some embodiments, different types of impact of these variant SNP genotypes to the Cannabis (CBD+THC) dosage and CBD/THC ratio can be considered. For example. Type I SNP genotypes respond differently to both THC and CBD. In one embodiment, 16 Type I SNP genotypes were identified, as illustrated in Table 7. It will be recognized, however, that other embodiments may include more or fewer Type I SNP genotypes.

As another example, Type II SNP genotypes respond differently to CBD only. In one embodiment, 5 Type II SNP genotypes were identified, as illustrated in Table 7. It will be recognized, however, that other embodiments may include more or fewer Type II SNP genotypes.

As a further example, Type II SNP genotypes respond differently to THC only. In one embodiment, 10 Type III SNP genotypes were identified, as illustrated in Table 7. It will be recognized, however, that other embodiments may include more or fewer Type III SNP genotypes.

Type I, Type II, and Type III SNP genotypes, alone or in combination, may lead to reduced or increased overall dosage of Cannabis (CBD+THC) and the ratio of CBD and THC in the treatments of conditions. The rate of dosage change from some genotypes provides a direct impact, whereas others may produce an indirect impact to gene expression and enzymatic activity.

As yet another example, Type IV SNP genotypes are associated with THC dependence only. In one embodiment, 13 Type IV SNP genotypes were identified, as illustrated in Table 7. It will be recognized, however, that other embodiments may include more or fewer Type IV SNP genotypes. These SNP genotypes may lead to reduced or increased THC dosage. In at least some embodiments, analysis of Type IV SNP genotypes may result in increase or reduction of the ratio of CBD to THC but not the overall Cannabis (CBD+THC) dosage in the treatments (see, for example, Table 7).

As described above, the base values are then modified by taking into account one or more of the four types of SNP genotypes to estimate unique individual genetic impacts of CBD and THC (or other cannabinoids) to arrive at suggested regimen CBD and THC dosages and a regimen CBD/THC ratio based on patient DNA tests.

Figure 3:
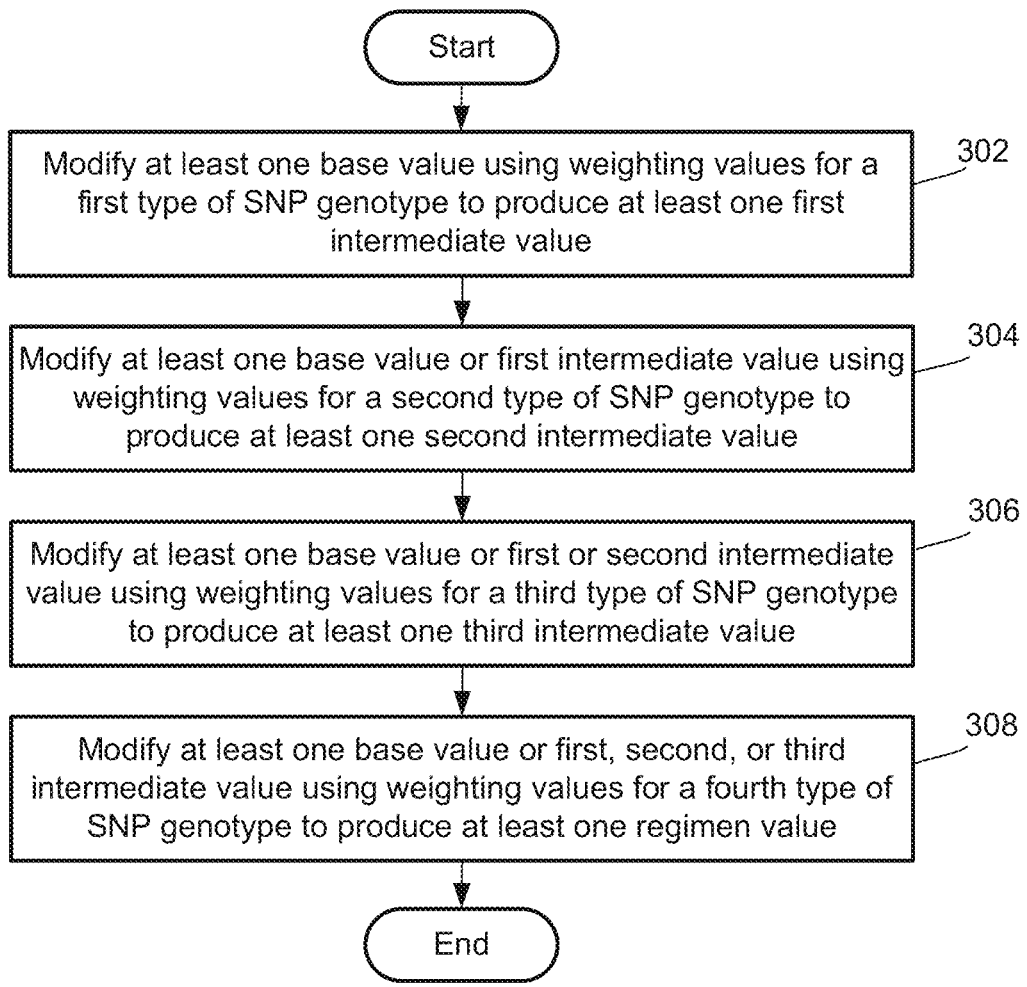
FIG. 3 is a flow chart of one embodiment of a method of modifying base values using weighting values to obtain regimen values, according to the invention.

FIG. 3 illustrates one embodiment of a method for modifying base values using weighting values (for example, step 208 in FIG. 2) using the four types of SNP genotypes. In step 302, at least one of the base values is modified using the weighting values for a first type of SNP genotype (for example, the Type I SNP genotypes described above) to produce at least one first intermediate value. In step 304, at least one base value or first intermediate value is modified using the weighting values for a second type of SNP genotype (for example, the Type II SNP genotypes described above) to produce at least one second intermediate value. In step 306, at least one base value or first or second intermediate value is modified using the weighting values for a third type of SNP genotype (for example, the Type III SNP genotypes described above) to produce at least one third intermediate value. In step 308, at least one base value or first, second, or third intermediate value is modified using the weighting values for a fourth type of SNP genotype (for example, the Type IV SNP genotypes described above) to produce at least one regimen value.

The flowchart in FIG. 3 illustrates a process for four types of SNP genotypes, but it will be understood that the process can be readily contract for two or three types of SNP genotypes by removing one or two steps or expanded for four or more types of SNP genotypes by adding steps similar to steps 304 or 306.

Figure 4:
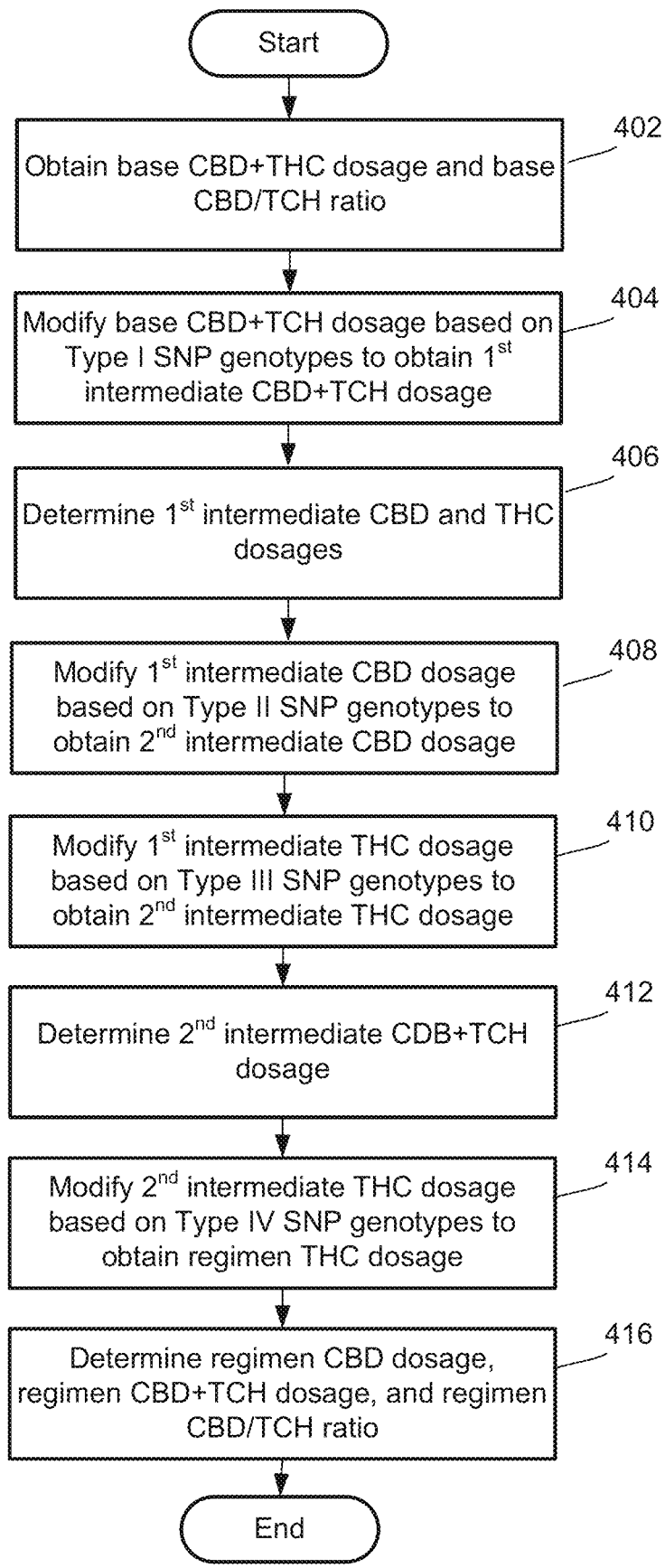
FIG. 4 is a flow chart of another embodiment of a method of modifying base values using weighting values to obtain regimen values, according to the invention.

FIG. 4 illustrates one embodiment of a process that implements the steps of FIG. 3 using the four types of SNP genotypes described above and provides an example of specific equations that can be used in this embodiment. It will be understood that these equations are examples and that other methods of modifying the base values to obtain the regimen values can be used. Table 8, below, provides an example of SNP genotypes and weighting values. Table 9, below, provides one specific case of determined SNP genotypes with the corresponding weighting values.

In step 402, specific base values (a base CBD+THC dosage and a base CBD/THC ratio) are obtained. In the equations below, D1 is the base CBD+THC dosage and R1 is the base CBD to THC Ratio, which are obtained in step 402 (see, also step 202 described above).

In step 404, the base CBD+THC dosage is modified based on the Type I SNP genotypes to obtain a first intermediate CBD+THC dosage. In at least some embodiments, D2 is the first intermediate CBD+THC dosage after factoring the individual impact of the obtained Type I SNP genotypes from the genetic test of the patient's DNA. D2 can be determined according to the following equation:

$$D2 = D1 \prod_{i=1}^{n} a_i$$

where
n=the number of Type 1 SNP genotypes tested and considered,
i=individual Type 1 SNP genotype, and
$a_i$=weighting value of the Type I SNP genotype i.

Alternatively, instead of limiting the calculation of D2 to Type I SNP genotypes, weighting values of all of the SNP genotypes can be used. It is likely, however, the weighting values of SNP genotypes other than the Type I SNP genotypes will have a value of 1 or a value near 1. Similarly, other steps described below include calculations using one of the types of SNP genotypes, but these steps can also be modified to include the weighting values for all of the SNP genotypes. In addition, as indicated above, in other embodiments, a summation function or exponential function can be used instead of the product function presented herein. This is also applicable to other equations presented below.

In Step 406, C2, the first intermediate CBD dosage after factoring the individual impact of Type I SNP genotypes, is determined according to the following equation:

$$C2 = D2 \left( \frac{R1}{R1+1} \right)$$

Also, T2, the first intermediate THC dosage after factoring the individual impact of Type I SNP genotypes is determined according to the following equation:

$$T2 = \frac{D2}{R1+1}$$

In step 408, the impact of the Type II SNP genotypes is introduced. C3, the second intermediate CBD dosage after factoring the individual impact of Type II SNP genotypes is given by the following equation:

$$C3 = C2 \prod_{i=1}^{n} b_i$$

where
n=the number of Type II SNP genotypes tested and considered,
i=individual Type II SNP genotype, and
$b_i$=individual impact of the Type II SNP genotype i.

In step 410, T3, the second intermediate THC dosage after factoring the individual impact of Type III SNP genotypes, is given by the following equation:

$$T3 = T2 \prod_{i=1}^{n} c_i$$

n=the number of Type III SNP genotypes tested and considered,
i=individual Type III SNP genotype, and
$c_i$=individual impact of Type III SNP genotype i.

In step 412, D3, the second intermediate CBD+THC dosage after factoring the individual impact of Types I-III SNP genotypes, is given by D3=C3+T3.

In step 414, the impact of the Type IV SNP genotypes is considered. T4, the regimen THC dosage after factoring the individual impact of Type IV SNP genotypes, is given by the following equation:

$$T4 = T3 \prod_{i=1}^{n} d_i$$

n=the number of Type IV SNP genotypes tested and considered,
i=individual Type IV SNP genotype, and
$d_i$=individual impact of the Type IV SNP genotype i.

These calculations then lead to the following dosages and ratios:

C4 is the regimen CBD dosage after factoring the individual impact of Type IV SNP genotypes and is given by: C4=D3−T4

$R_f$ is the regimen CBD to THC ratio after factoring the impact of SNP genotypes and is given by: $R_f$=C4/T4

$D_f$ is the regimen CBD+TCH dosage after factoring the impact of SNP genotypes and is given by: $D_f$=C4+T4.

In step 416, the regimen CBD dosage, regimen CBD+THC dosage, and regimen CBD/THC ratio are determined. Table 9 illustrates the base, intermediate, and regimen values for three examples of different treatments.

The final recommendations of the CBD+THC dosage and the CBD to THC ratio can be provided to a clinician or patient in, for example, a report or recommendation card. In at least some embodiments, details of the SNP genotypes (e.g., genetic variants) and their impacts on the dosage and ratio may also be delivered to a clinician or patient in the same or different report.

EXAMPLE

Figure 5:
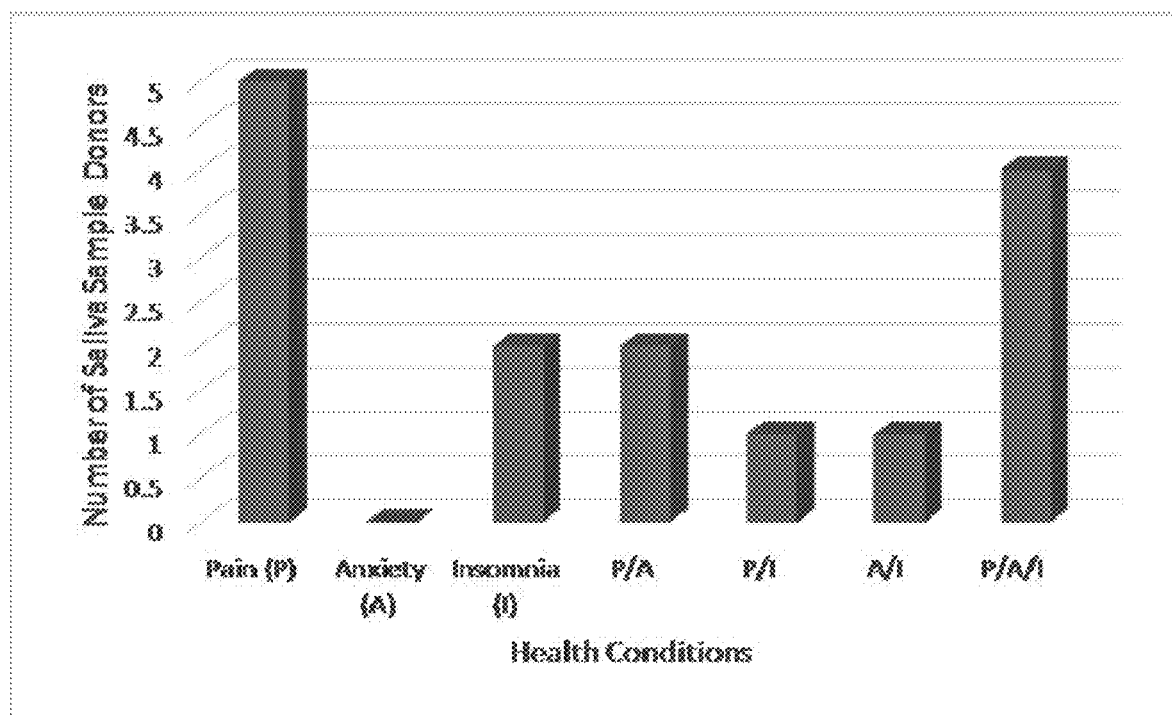
FIG. 5 is graph of different health conditions for participants in a study.

Selected variants and the algorithm were used to predict the CBD/THC dosage in treating different conditions or combinations of different health conditions including pain, anxiety, and insomnia. Samples were obtained from participants who were exploring *Cannabis* solutions to resolve either the individual conditions of pain (P), anxiety (A), or insomnia (I), or combinations of these individual conditions: pain/anxiety (P/A), pain/insomnia (P/I), anxiety/insomnia (A/I), or all three conditions (P/A/I). FIG. 5 shows the number of donors showing interest in each one of these health conditions.

Figure 6:
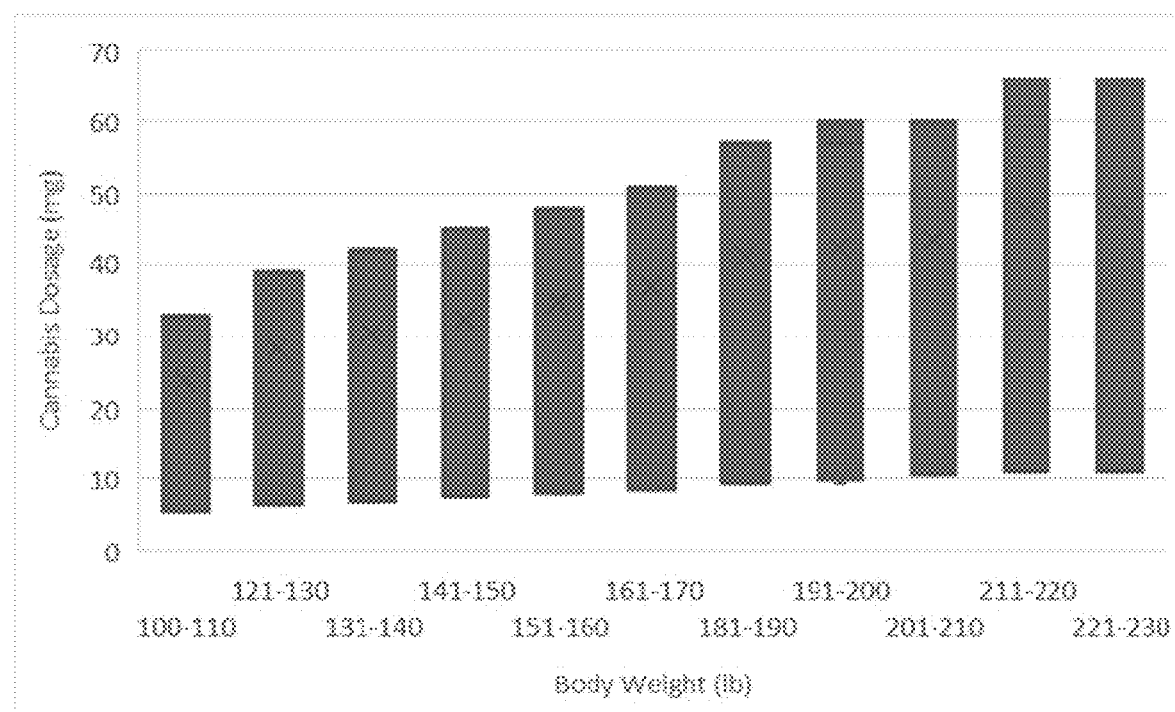
FIG. 6 is a graph of *Cannabis* dosage versus body weight for the participants in the study based on conventional dosage determinations.

Saliva samples were processed for DNA preparation, PCR and sequencing, and for the subsequent identification and analysis of the gene variants. The variant Linkage Disequilibrium and the genotype association to the health conditions was analyzed as illustrated in FIG. 6. Linkage Disequilibrium (LD) tests (see Reference 53) verified several groups of associated variants from common genes (e.g. variant rs 2229579, rs35761398, and rs2501432 from the CNR2 gene; rs279871, rs279856, and rs279826 from the GABRA2 gene; and rs806368, rs12720071, and rs1049353 from the CNR1 gene) as well as associated variants from different genes (e.g. rs12199654 from MAPK14 and rs 12720071 and other SNP variants from CNR1) indicating high quality variant genotype data were generated in this study. A number of variants were associated with statistical significance with pain and with other health conditions suggesting highly quality genetic variants were selected in this study (see, Table 10 below).

In addition to the variants demonstrating association to different health conditions, a number of different variants that may impact the reception, signaling, as well as metabolism of cannabinoids, and thus lead to different dosage requirement for individuals were also identified from every saliva sample (see Table 11 that presents examples of variant alleles identified from two saliva samples 1002 and 1013).

To determine the dosage of Cannabis, it is a common practice to start by weighting in body weight and different health conditions of concern. Conventionally, larger body weight leads to an increase in dosage, whereas different health conditions also result in variation of the dosage for a given body weight. As an example, conventionally, a microdose is considered effective for insomnia, but a standard to macro-dose may be recommended for pain and anxiety conditions. For the 19 participant samples analyzed in this Example, standard dose recommendations for their different body weight and different health concern are presented in FIG. 6.

Figure 7:
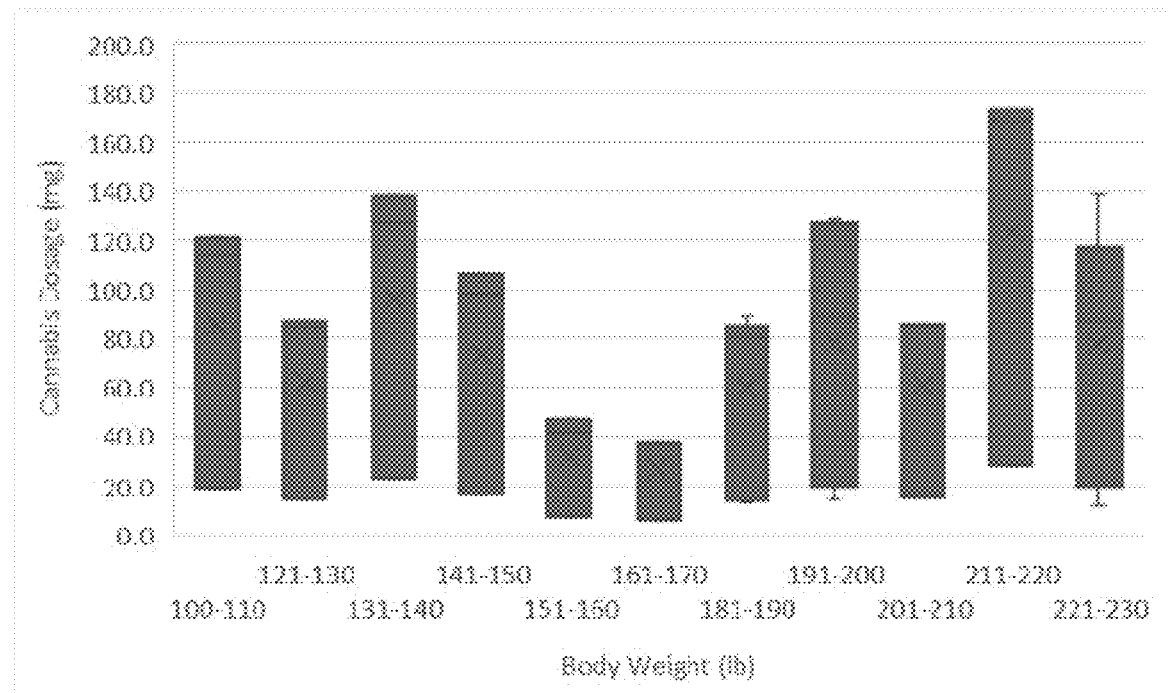
FIG. 7 is a graph of *Cannabis* dosage versus body weight for the participants utilizing patient DNA information to provide a personalized cannabinoid treatment regimen, according to the invention.

In contrast, a genotyping procedure, as described herein, identified a unique set of 5 to 12 variants, see Table 12, likely impacting the Cannabis dosage for each participants. The genetic impact of the variants on the dosage of CBD and THC were calculated using the algorithm described above. Results, presented in FIG. 7, showed highly differentiated and personalized CBD/THC dosage comparing to the standard dose recommendations, suggesting that this selected group of variants and the dosage calculating algorithm is a useful approach to predicting the CBD/THC dosage for the health conditions described here. After delivering the genetic report and dosage recommendation to the saliva donors, follow-up interviews all returned positive feedbacks from these donors.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the manufacture and use of the invention. Since many embodiments of the invention can be made without departing from the spirit and scope of the invention, the invention also resides in the claims hereinafter appended.

REFERENCES (CITED IN THE TEXT AND TABLES AND INCORPORATED HEREIN BY REFERENCE IN THEIR ENTIRETIES)

1. Agrawal A, Edenberg H J, Foroud T, Bierut L J, Dunne G, Hinrichs A L, Nurnberger J I, Crowe R, Kuperman S, Schuckit M A, Begleiter H, Porjesz B, Dick D M. Association of GABRA2 with drug dependence in the collaborative study of the genetics of alcoholism sample. Behav Genet. 2006; 36:640-50.
2. Albert P R. Transcriptional regulation of the 5-HT1A receptor: implications for mental illness. Philos Trans R Soc Lond B Biol Sci. 2012 Sep. 5; 367(1601):2402-15. doi: 10.1098/rstb.2011.0376.
3. Baune B T, Hohoff C, Roehrs T, Deckert J, Arolt V, Domschke K. Serotonin receptor 1A-1019C/G variant: impact on antidepressant pharmacoresponse in melancholic depression? Neurosci Lett. 2008 May 9; 436(2):111-5. doi: 10.1016/j.neulet.2008.03.001. Epub 2008 Mar. 6. PMID: 18387740
4. Benyamina A. Bonhomme-Faivre L, Picard V, Sabbagh A, Richard D, Blecha L, Rahioni H, Karila L, Lukasiewicz M, Farinotti R, Picard V, Marill C, Reynaud M. Association between ABCB1 C3435T polymorphism and increased risk of Cannabis dependence. Prog Neuropsychopharmacol Biol Psychiatry. 2009; 33:1270-4.
5. Bhattacharyya S, Iyegbe C, Atakan Z, Martin-Santos R, Crippa J A, Xu X, Williams S, Brammer M, Rubia K, Prata D, Collier D A, McGuire P K. Protein kinase B (AKT1) genotype mediates sensitivity to Cannabis-induced impairments in psychomotor control. Psychol Med. 2014 November; 44(15):3315-28.
6. Binder A, May D, Baron R, Maier C, Tölle T R, Treede R D, Berthele A, Faltraco F, Flor H, Gierthmühlen J, Haenisch S, Huge V, Magerl W, Maihöfner C, Richter H, Rolke R, Scherens A, Uçeyler N, Ufer M, Wasner G, Zhu J, Cascorbi I. Transient receptor potential channel polymorphisms are associated with the somatosensory function in neuropathic pain patients. PLOS One. 2011 Mar. 29; 6(3):e17387. doi: 10.1371/jourual.pone.0017387. PMID: 21468319
7. Buttari F, Zagaglia S, Marciano L, Albanese M, Landi D, Nicoletti C G, Mercuri N B, Silvestrini M, Provinciali L, Marfia G A, Mori F, Centonze D. TRPV1 polymorphisms and risk of interferon $β$-induced flu-like syndrome in patients with relapsing-remitting multiple sclerosis. J Neuroimmunol. 2017 Apr. 15; 305:172-174.
8. Carey C E, Agrawal A, Zhang B, Conley E D, Degenhardt L, Heath A C, Li D, Lynskey M T, Martin N G, Montgomery G W, Wang T, Bierut L J, Hariri A R, Nelson E C, Bogdan R. Monoacylglycerol lipase (MGLL) polymorphism rs604300 interacts with childhood adversity to predict Cannabis dependence symptoms and amygdala habituation: Evidence from an endocannabinoid system-level analysis. J Abnorm Psychol. 2015 November; 124 (4): 860-77.
9. Carrasquer A, Nebane N M, Williams W M, Song Z H. Functional consequences of nonsynonymous single nucleotide polymorphisms in the CB2 cannabinoid receptor. Pharmacogenet Genom. 2010; 20:157-66.
10. Chen, R., Zhang, J., Fan, N., Teng. Z. Q., Wu. Y., Yang, H., et al. (2013). Delta9-THC-caused synaptic and memory impairments are mediated through COX-2 signaling. Cell, 155, 1154e1165.

11. Chou W Y, Wang C H, Liu P H, Liu C C, Tseng C C, Jawan B. Human opioid receptor A118G polymorphism affects intravenous patient-controlled analgesia morphine consumption after total abdominal hysterectomy. Anesthesiology 2006; 105:334-7.

12. Eum S, Lee A M, Bishop J R. Pharmacogenetic tests for antipsychotic medications: clinical implications and considerations. Dialogues Clin Neurosci. 2016 September; 18(3):323-337. Review. PMID: 27757066

13. Fabbri C, Porcelli S, Serretti A. From pharmacogenetics to pharmacogenomics: the way toward the personalization of antidepressant treatment. Can J Psychiatry. 2014 February; 59(2):62-75. Review. PMID: 24881125

14. Forstenpointner J, Forster M, May D, Hofschulte F, Cascorbi I, Wasner G, Gierthmuhlen J, Baron R. Short Report: TRPV1-polymorphism 1911 A>G alters capsaicin-induced sensory changes in healthy subjects. PLOS One. 2017 Aug. 17; 12(8):e0183322. doi: 10.1371/journal.pone.0183322. eCollection 2017.

15. Furuta T, Ohashi K, Kamata T, Takashima M, Kosuge K, Kawasaki T, Hanai H, Kubota T, Ishizaki T, Kaneko E. Effect of genetic differences in omeprazole metabolism on cure rates for *Helicobacter pylori* infection and peptic ulcer. Ann Intern Med. 1998 Dec. 15; 129(12):1027-30.

16. Galecki P, Florkowski A, Bieńkiewicz M, Szemraj J. Functional polymorphism of cyclooxygenase-2 gene (G-765C) in depressive patients. Neuropsychobiology. 62(2), 116-120 (2010).

17. Gong X D, Wang J Y, Liu F, Yuan H H, Zhang W Y, Guo Y H, Jiang B. Gene polymorphisms of OPRM1 A118G and ABCB1 C3435T may influence opioid requirements in Chinese patients with cancer pain. Asian Pac J Cancer Prev. 2013; 14(5):2937-43. PMID: 23803057

18. Hammerschlag A R, Stringer S, de Leeuw C A, Sniekers S, Taskesen E, Watanabe K. Blanken T F, Dekker K, Te Lindert B H W, Wassing R, Jonsdottir I, Thorleifsson G, Stefansson H, Gislason T, Berger K, Schormair B, Wellmann J, Winkelmann J, Stefansson K, Oexle K, Van Someren E J W, Posthuma D. Genome-wide association analysis of insomnia complaints identifies risk genes and genetic overlap with psychiatric and metabolic traits. Nat Genet. 2017 November; 49(11):1584-1592. doi: 10.1038/ng.3888. Epub 2017 Jun. 12. PMID: 28604731

19. Han S, Yang B Z, Kranzler H R, Oslin D, Anton R, Farrer L A, Gelernter J. Linkage analysis followed by association show NRG1 associated with *Cannabis* dependence in African Americans. Biol Psychiatry. 2012; 72:637-44.

20. Ho B C, Wassink T H, Ziebell S, Andreasen N C. Cannabinoid receptor 1 gene polymorphisms and marijuana misuse interactions on white matter and cognitive deficits in schizophrenia. Schizophrenia Research. 2011; 128:66-75. [PubMed: 21420833]

21. Holst S C, Valomon A, Landolt H P. Sleep Pharmacogenetics: Personalized Sleep-Wake Therapy. Annu Rev Pharmacol Toxicol. 2016; 56:577-603. doi: 10.1146/annurev-pharmtox-010715-103801. Epub 2015 Nov. 2.

22. Hopfer C J, Young S E, Purcell S, Crowley T J, Stallings M C, Corley R P, Rhee S H, Smolen A, Krauter K, Hewitt J K. Ehringer M A. *Cannabis* receptor haplotype associated with fewer *Cannabis* dependence symptoms in adolescents. Am J Med Genet B Neuropsychiatr Genet. 2006; 141B: 895-901.

23. Howlett A C, Abood M E. CB1 and CB2 Receptor Pharmacology. Adv Pharmacol. 2017; 80:169-206. doi: 10.1016/bs.apha.2017.03.007.

24. Hryhorowicz S, Walczak M, Zakerska-Banaszak O, Słomski R, Skrzypczak-Zielińska M. Pharmacogenetics of Cannabinoids. Eur J Drug Metab Pharmacokinet. 2018 February; 43(1):1-12. doi: 10.1007/s13318-017-0416-z. Review.

25. Ishiguro H, Onaivi E S, Horinchi Y, Imai K, Komaki G, Ishikawa T, Suzuki M, Watanabe Y, Ando T, Higuchi S, Arinami T. Functional polymorphism in the GPR55 gene is associated with anorexia nervosa. Synapse. 2011 February; 65(2):103-8. doi: 10.1002/syn.20821.

26. Kebir O, Lafaye G, Blecha L, Chaumette B, Mouaffak F, Laqueille X, Benyamina A. ABCB1 C3435T polymorphism is associated with tetrahydrocannabinol blood levels in heavy *Cannabis* users. Psychiatry Res. 2018 April; 262:357-358. doi: 10.1016/j.psychres.2017.09.006. Epub 2017 Sep. 9.

27. Ketcherside A, Noble L J, Mcintyre C K, Filbey F M. Cannabinoid Receptor 1 Gene by *Cannabis* Use Interaction on CB1 Receptor Density. *Cannabis* Cannabinoid Res. 2017 Aug. 1; 2(1):202-209.

28. Kim H, Mittal D P, Iadarola M J, Dionne R A (2006). Genetic predictors for acute experimental cold and heat pain sensitivity in humans. J Med Genet 43: e40.

29. Ko T M, Wong C S, Wu J Y, Chen Y T. Pharmacogenomics for personalized pain medicine. Acta Anaesthesiol Taiwan. 2016 March; 54 (1): 24-30. doi: 10.1016/j.aat.2016.02.001. Epub 2016 Mar. 11. Review. PMID: 26976339

30. Lazary J, Lazary A, Gonda X, Benko A, Molnar E, Hunyady L, Juhasz G, Bagdy G. Promoter variants of the cannabinoid receptor 1 gene (CNR1) in interaction with 5-HTTLPR affect the anxious phenotype. Am J Med Genet B Neuropsychiatr Genet, 2009; 150B: 1118-1127.

31. Leinow L, Birnbaum J. CBD. A Patient's Guide to Medical *Cannabis*. 2017 North Atlantic Books, Berkeley, California.

32. Lötsch J, Geisslinger G. Pharmacogenetics of new analgesics. Br J Pharmacol. 2011 June; 163(3):447-60. doi: 10.1111/j.1476-5381.2010.01074.x. Review.

33. Maple K E, McDaniel K A, Shollenbarger S G, Lisdahl K M. Dose-dependent *Cannabis* use, depressive symptoms, and FAAH genotype predict sleep quality in emerging adults: a pilot study. Am J Drug Alcohol Abuse. 2016 July; 42 (4): 431-40. doi: 10.3109/00952990.2016.1141913.

34. McMahon F J, Buervenich S, Charney D, Lipsky R. Rush A J, Wilson A F, Soraut A J M, Papanicolaou G J, Laje G, Fava M, Trivedi M H, Wisniewski S R, Manji H. Variation in the gene encoding the serotonin 2A receptor is associated with outcome of antidepressant treatment. Am J Hum Genet. 2006 May; 78(5):804-814. doi: 10.1086/503820. Epub 2006 Mar. 20.

35. Mitjans M, Serretti A, Fabbri C et al. Screening genetic variability at the CNR1 gene in both major depression etiology and clinical response to citalopram treatment. Psychopharmacology (Berl.) 227 (3), 509-519 (2013).

36. Onwuameze O E, Nam K W, Epping E A, Wassink T H, Ziebell S, Andreasen N C, Ho B C. MAPK14 and CNR1 gene variant interactions: effects on brain volume deficits in schizophrenia patients with marijuana misuse. Psychol Med. 2013; 43:619-31.

37. Peiró A M, Planelles B, Juhasz G. Bagdy G, Libert F, Eschalier A, Busserolles J, Sperlagh B, Llerena A. Pharmacogenomics in pain treatment. Drug Metab Pers Ther. 2016 Sep. 1; 31(3):131-42. doi: 10.1515/dmpt-2016-0005.

38. Sagnelli C, Uberti-Foppa C, Hasson H, Bellini G, Minichini C, Salpietro S, et al. (2017) Cannabinoid receptor 2-63 RR variant is independently associated with severe necroinflammation in HIV/HCV coinfected patients. PLOS ONE 12 (7): e0181890. doi.org/10.1371/journal.pone.0181890

39. Schroeder F, McIntosh A L, Martin G G, Huang H, Landrock D, Chung S, Landrock K K, Dangott L J, Li S, Kaczocha M, Murphy E J, Atshaves B P, Kier A B. Fatty Acid Binding Protein-1 (FABP1) and the Human FABP1 T94A Variant: Roles in the Endocannabinoid System and Dyslipidemias. Lipids. 2016 June; 51(6):655-76.

40. Sipe J C, Chiang K, Gerber A L, Beutler E, Cravatt B F. A missense mutation in human fatty acid amide hydrolase associated with problem drug use. Proc Natl Acad Sci USA. 2002; 99: 8394-9.

41. Stout S M, Cimino N M. Exogenous cannabinoids as substrates, inhibitors, and inducers of human drug metabolizing enzymes: a systematic review. Drug Metab Rev. 2014 February; 46(1):86-95. doi: 10.3109/03602532.2013.849268. Epub 2013 Oct. 25. Review. PMID: 24160757

42. Tahamtan A, Samieipoor Y, Nayeri F S, Rahbarimanesh A A, Izadi A. Rashidi-Nezhad A, Tavakoli-Yaraki M, Farahmand M, Bont L, Shokri F. Mokbatri-Azad T, Salimi V. Effects of cannabinoid receptor type 2 in respiratory syncytial virus infection in human subjects and mice. Virulence. 2017 Oct. 9:0. doi: 10.1080/21505594.2017.1389369.

43. Uhr M, Tontsch A, Namendorf C, et al. Polymorphisms in the drug transporter gene ABCB1 predict antidepressant treatment response in depression. Neuron. 2008; 57(2):203-209.

44. Woo J H, Kim H, Kim J H, Kim J G. Cannabinoid receptor gene polymorphisms and bone mineral density in Korean postmenopausal women. Menopause. 2015 May; 22(5):512-9. doi: 10.1097/GME.0000000000000339.

45. Zajkowska Z E, Englund A, Zunszain P A. Towards a personalized treatment in depression: endocannabinoids, inflammation and stress response. Pharmacogenomics. 2014 April; 15(5):687-98.

46. Zhang P W, Ishiguro H, Ohtsuki T, Hess J, Carillo F. Walther D, Onaivi E S, Arinami T, Ubl G R. Human cannabinoid receptor 1: 5′ exons, candidate regulatory regions, polymorphisms, haplotypes and association with polysubstance abuse. Mol Psychiatry. 2004; 9(10):916-931. [PubMed: 15289816].

47. Haughey H M I, Marshall E, Schacht J P, Louis A, Hutchison K E. Marijuana withdrawal and craving: influence of the cannabinoid receptor 1 (CNR1) and fatty acid amide hydrolase (FAAH) genes. Addiction. 2008 October; 103(10):1678-86. doi: 10.1111/j.1360-0443.2008.02292.x. Epub 2008 Aug. 14.

48. Dobrinas M, Crettol S, Oneda B, Lahyani R, Rotger M, Choong E, Lubomirov R, Csajka C, Eap C B. Contribution of CYP2B6 alleles in explaining extreme(S)-methadone plasma levels: a CYP2B6 gene resequencing study. Pharmacogenet Genomics. 2013 February; 23 (2): 84-93. doi: 10.1097/FPC.0b013e32835cb2e2. PMID: 23249875

49. Pardini M I, Krueger F, Koenigs M, Raymont V, Hodgkinson C, Zoubak S, Goldman D, Grafinan J. Fatty-acid amide hydrolase polymorphisms and post-traumatic stress disorder after penetrating brain injury. Transl Psychiatry. 2012 Jan. 31:2:e75. doi: 10.1038/tp.2012.1.

50. Horstmann S1, Lucae S, Menke A, Hennings J M, Ising M, Roeske D, Müller-Myhsok B, Holsboer F, Binder E B. Polymorphisms in GRIK4, HTR2A, and FKBP5 show interactive effects in predicting remission to antidepressant treatment. Neuropsychopharmacology. 2010 February; 35(3):727-40. doi: 10.1038/upp.2009.180. Epub 2009 Nov. 18.

51. Deuschle M I, Schredl M, Schilling C, Wüst S, Frank J, Witt S H, Rietschel M, Buckert M, Meyer-Lindenberg A, Schulze T G. Association between a serotonin transporter length polymorphism and primary insomnia. Sleep. 2010 March; 33(3):343-7.

52. Smith D R, Stanley C M, Foss T, Boles R G, MeKernan K. Rare genetic variants in the endocannabinoid system genes CNR1 and DAGLA are associated with neurological phenotypes in humans. PLOS One. 2017 Nov. 16; 12(11):e0187926. doi: 10.1371/journal.pone.0187926. eCollection 2017.

53. Shi Y Y, He L. SHEsis, a powerful software platform for analyses of linkage disequilibrium, haplotype construction, and genetic association at polymorphism loci. Cell Res. 2005 February; 15(2):97-8.

TABLE 1

SNPs from genes of endocannabinoid systems and response to cannabinoids

| Target Conditions | Function | Category | Gene | SNP number | Nucleotide Change | Reference(s) |
|---|---|---|---|---|---|---|
| Cannabis Response | Receptor | Receptor | CNR1 | rs806380 | c.−63−9597 T > C | Ref. #24 |
| Cannabis Response | Receptor | Receptor | CNR1 | rs806368 | c.*3475 A > G | Ref. #24 |
| Cannabis Response | Receptor | Receptor | CNR1 | rs1049353 | c.1359 A > G | Ref. #24 |
| Cannabis Response | Receptor | Receptor | CNR1 | rs2180619 | | Refs. #46 and #23 |
| Cannabis Response | Receptor | Receptor | CNR1 | rs2023239 | | Refs. #47 and #27 |
| Cannabis Response | Receptor | Receptor | CNR2 | rs2501432/rs35761398 (Same locus) | | Refs. #24, #38, #42, and #45 |
| Cannabis Response | Receptor | Receptor | CNR2 | rs2229579 | His316Tyr | Ref. #24 |
| Cannabis Response | Transport | Transporters | ABCB1 | rs1045642 | 3435C > T | Ref. #24 |
| Cannabis Response | Biotransformation | Enzyme | FAAH | rs34420 | 385C > A | Ref. #24 |
| Cannabis Response | Biotransformation | Enzyme | COMT | rs4680 | 472A > G | Ref. #24 |
| Cannabis Response | Others | Receptor | GABRA2 | rs279858 | 231A > G | Ref. #1 |
| Cannabis Response | Others | Receptor | GABRA2 | rs279871 | | Ref. #1 |
| Cannabis Response | Others | Receptor | GABRA2 | rs279826 | | Ref. #1 |
| Cannabis Response | Others | Signaling | NRG1 | rs17664708 | 122−16329C > T | Ref. #19 |
| Cannabis Response | Enzymes | Enzyme | CYP1A2 | rs762551 | | Ref. #21 |
| Cannabis Response | Enzymes | Enzyme | CYP2C9 | rs1057910 | | Ref. #24 |
| Cannabis Response | Enzymes | Enzyme | CYP2C19 | rs4244285 | | Ref. #24 |
| Cannabis Response | Enzymes | Enzyme | CYP3A4 | rs67666821 | | Ref. #24 |
| Cannabis Response | Enzymes | Enzyme | CYP3A4 | rs4646438 | | Ref. #24 |

TABLE 1-continued

SNPs from genes of endocannabinoid systems and response to cannabinoids

| Target Conditions | Function | Category | Gene | SNP number | Nucleotide Change | Reference(s) |
|---|---|---|---|---|---|---|
| *Cannabis* Response | Signaling | Signaling | MAPK14 | rs12199654 | | Ref. #24 |
| *Cannabis* Response | Signaling | Signaling | NRG1 | rs17664708 | | Ref. #24 |

TABLE 2

SNPs associated responses of pain treatment

| Target Conditions | Functions | Category | Gene | SNP number | Nucleotide Change | Reference(s) |
|---|---|---|---|---|---|---|
| Pain medicine | Receptors | Receptor | TRPV1 | rs222747 | | Ref. #7 |
| Pain medicine | Receptors | Receptor | TRPV1 | rs8065080 | | Ref. #14 |
| Pain medicine | Receptors | Transporters | FABP1 | rs2241883 | | Ref. #39 |
| Pain medicine | Receptors | Receptor | OPRM1 | rs1799971 | A118G | Ref. #37 |
| Pain medicine | Transport | Transporters | ABCB1 | rs1045642 | 3435C > T | Ref. #29 |
| Pain medicine | Biotransformation | Enzyme | COMT | rs4680 | 472A > G | Ref. #37 |
| Pain medicine | Metabolism | Enzyme | CYP2D6 | rs16947 | CYP2D6*1/*2 | Ref. #29 |
| Pain medicine | Metabolism | Enzyme | CYP2D6 | rs1135840 | CYP2D6*1/*2 | Ref. #29 |
| Pain medicine | Metabolism | Enzyme | CYP2D6 | rs35742686 | CYP2D6*3/*3 | Ref. #29 |
| Pain medicine | Metabolism | Enzyme | CYP2B6 | rs35303484 | CYP2B6*11; c136A > G; M46V | Ref. #48 |
| Pain medicine | Metabolism | Enzyme | CYP2C9 | rs1057910 | CYP2C9*3/*3 | Ref. #29 |
| Pain medicine | Immune Hypersensitivity | Signaling | HLA | rs3909184 | HLA-B*1502 | Ref. #29 |
| Pain medicine | Immune Hypersensitivity | Signaling | HLA | rs2844682 | HLA-B*1502 | Ref. #29 |
| Pain medicine | Immune Hypersensitivity | Signaling | HLA | rs1061235 | HLA-A*3101 | Ref. #29 |
| Pain medicine | Immune Hypersensitivity | Signaling | HLA | rs2734331 | HLA-B*3801 | Ref. #29 |
| Pain medicine | Immune Hypersensitivity | Signaling | HLA | (Q126H) | HLA-DBQ1 (126Q) | Ref. #29 |
| Pain medicine | Immune Hypersensitivity | Signaling | HLA | A158T | KLA-B(158T) | Ref. #29 |

TABLE 3

SNPs associated with anxiety/depression and responses of treatment

| Target Conditions | Functions | Category | Gene | SNP number | Reference(s) |
|---|---|---|---|---|---|
| Depression/anxiety | Endocannabinoids | Receptor | CNR1 | rs2180619 | Refs. #46, #23, and #30 |
| Depression/anxiety | Endocannabinoids | Receptor | CNR1 | rs1049353 | Ref. #45 |
| Depression/anxiety | Endocannabinoids | Receptor | CNR1 | rs806368 | Ref. #45 |
| Depression/anxiety | Endocannabinoids | Receptor | CNR1 | rs806371 | Ref. #45 |
| Depression/anxiety | Endocannabinoids | Receptor | CNR1 | rs2023239 | Ref. #45 |
| Depression/anxiety | Endocannabinoids | Receptor | CNR1 | rs806379 | Ref. #45 |
| Depression/anxiety | Endocannabinoids | Receptor | CNR1 | rs1535255 | Ref. #45 |
| Depression/anxiety | Endocannabinoids | Receptor | CNR1 | rs806369 | Ref. #45 |
| Depression/anxiety | Endocannabinoids | Receptor | CNR1 | rs4707436 | Ref. #45 |
| Depression/anxiety | Endocannabinoids | Receptor | CNR1 | rs12720071 | Ref. #45 |
| Depression/anxiety | Endocannabinoids | Receptor | CNR1 | rs806366 | Ref. #45 |
| Depression/anxiety | Endocannabinoids | Receptor | CNR1 | rs7766029 | Ref. #45 |
| Depression/anxiety | Endocannabinoids | Receptor | CNR2 | rs2501431 | Ref. #45 |
| Depression/anxiety | Endocannabinoids | Enzyme | FAAH | rs2295633 | Refs. #49 and #45 |
| Depression/anxiety | Endocannabinoids | Enzyme | FAAH | rs324420 | Refs. #33 and #45 |
| Depression/anxiety | Endocannabinoids | Signaling | AKT1 | rs1130233 | Ref. #5 |
| Depression/anxiety | Autoimmune | Signaling | IL-1β | rs16944 | Ref. #45 |
| Depression/anxiety | Autoimmune | Signaling | IL-1β | rs1143627 | Ref. #45 |
| Depression/anxiety | Autoimmune | Signaling | IL-1β | rs1143633 | Ref. #45 |
| Depression/anxiety | Autoimmune | Signaling | IL-1β | rs1143643 | Ref. #45 |
| Depression/anxiety | Autoimmune | Enzyme | COX-2 | rs4648308 | Ref. #45 |
| Depression/anxiety | Autoimmune | Enzyme | COX-2 | rs20417 | Ref. #45 |
| Depression/anxiety | HPA Axis | Receptor | NR3C1 | rs6189 | Ref. #45 |
| Depression/anxiety | HPA Axis | Receptor | NR3C1 | rs6190 | Ref. #45 |
| Depression/anxiety | HPA Axis | Receptor | NR3C1 | rs41423247 | Ref. #45 |
| Depression/anxiety | HPA Axis | Receptor | NR3C1 | rs1876828 | Ref. #13 |
| Depression/anxiety | HPA Axis | Receptor | NR3C1 | rs242939 | Ref. #13 |
| Depression/anxiety | HPA Axis | Receptor | NR3C1 | rs242941 | Ref. #13 |
| Depression/anxiety | HPA Axis | Receptor | NR3C1 | rs6198 | Ref. #45 |
| Depression/anxiety | HPA Axis | Enzyme | FKBP5 | rs4713916 | Ref. #45 |
| Depression/anxiety | HPA Axis | Enzyme | FKBP5 | rs1360780 | Ref. #45 |
| Depression/anxiety | Glutamatergic System | Signaling | GRIK4 | rs12800734 | Ref. #50 |

TABLE 3-continued

SNPs associated with anxiety/depression and responses of treatment

| Target Conditions | Functions | Category | Gene | SNP number | Reference(s) |
|---|---|---|---|---|---|
| Depression/anxiety | Glutamatergic System | Signaling | GRIK4 | rs1954787 | Ref. #50 |
| Depression/anxiety | Serotoninergic System | Receptor | HTR2A | rs17288723 | Ref. #50 |
| Depression/anxiety | Serotoninergic System | Transporters | SLC6A4 | 5HTTLPR | Refs. #13 and #51 |
| Depression/anxiety | Serotoninergic System | Transporters | SLC6A4 | STin2 VNTR | Ref. #13 |
| Depression/anxiety | Serotoninergic System | Receptor | HTR1A | rs6295 | Refs. #13 and #3 |
| Depression/anxiety | Serotoninergic System | Receptor | HTR1B | rs62898 | Ref. #13 |
| Depression/anxiety | Serotoninergic System | Receptor | HTR2A | rs6311 | Ref. #13 |
| Depression/anxiety | Serotoninergic System | Receptor | HTR2A | rs7997012 | Ref. #13 |
| Depression/anxiety | Serotoninergic System | Receptor | HTR2A | rs1928040 | Ref. #13 |
| Depression/anxiety | Serotoninergic System | Enzyme | TPH1 | rs1800532 | Ref. #13 |
| Depression/anxiety | Serotoninergic System | Enzyme | TPH2 | rs120074175 | Ref. #13 |
| Depression/anxiety | Noradrenergic System | Enzyme | COMT | rs4680 | Ref. #13 |
| Depression/anxiety | Noradrenergic System | Enzyme | MAOA | VNTR 1.2 kb upstream coding sequence | Ref. #13 |
| Depression/anxiety | Noradrenergic System | Transporters | SLC6A2 | rs5569 | Ref. #13 |
| Depression/anxiety | Dopaminergic System | Transporters | SLC6A3 | 3'UTR 40-bp VNTR | Ref. #13 |
| Depression/anxiety | Signaling and Growth Factors | Signaling | BDNF | rs6265 | Ref. #13 |
| Depression/anxiety | Signaling and Growth Factors | Signaling | GNB3 | rs5443 | Ref. #13 |
| Depression/anxiety | Enzymes | Enzyme | ACE | Insertion or deletion | Ref. #13 |
| Depression/anxiety | Enzymes | Enzyme | GSK3B | rs334558 | Ref. #13 |
| Depression/anxiety | Pharmacokinetics | Transporters | ABCB1 | rs2032582 | Refs. #13 and #43 |
| Depression/anxiety | Pharmacokinetics | Transporters | ABCB1 | rs1045642 | Ref. #26 |

TABLE 4

SNPs associated insomnia and responses of treatment

| Target Conditions | Functions | Category | Gene | SNP number | Reference(s) |
|---|---|---|---|---|---|
| Sleep Disorder | Endocannabinoids | Receptor | CNR1 | rs78783387 | Ref. #26 |
| Sleep Disorder | Endocannabinoids | Enzyme | FAAH | rs324420 | Refs. #33, #45 |
| Sleep Disorder | Enzymes | Enzyme | CYP2D6 | Gene Copy Nos. | Ref. #21 |
| Sleep Disorder | Enzymes | Enzyme | CYP2C19 | Various Alleles | Ref. #21 |
| Sleep Disorder | Enzymes | Enzyme | CYP3A4 | Various Alleles | Ref. #21 |
| Sleep Disorder | Serotoninergic System | Receptor | HTR2A | rs6311 | Ref. #21 |
| Sleep Disorder | Enzymes | Enzyme | CYP1A2 | rs762551 | Ref. #21 |
| Sleep Disorder | Melatoninergic System | Receptor | MTNR1d | rs2119882 | Ref. #21 |
| Sleep Disorder | Organic Cation | Transporters | SLC22A4 | rs195152 | Ref. #21 |
| Sleep Disorder | Serotoninergic System | Receptor | HTR1B | rs130060 | Ref. #21 |
| Sleep Disorder | Serotoninergic System | Receptor | HTR2A | rs6313 | Ref. #21 |
| GWAS/Insomnia | NA | | SCFD2 | rs574753165 | Ref. #18 |
| GWAS/Insomnia | NA | | WDR27 | rs13192566 | Ref. #18 |
| GWAS/Insomnia | NA | | MEIS1 | rs113851554 | Ref. #18 |
| GWAS/Insomnia | NA | | WDR27 | rs71554396 | Ref. #18 |
| GWAS/Insomnia | NA | | CEP152 | rs2725544 | Ref. #18 |

TABLE 5

Primers designed for selected SNPs for testing

| Genes | SNPs | Notes | Chromosome Position | Forward Primer | Reverse Primer |
|---|---|---|---|---|---|
| OPRM1 | rs1799971 | NC_000006.12:g.154039662 A > G | 154360797 | AAAAGTCTCGGTGCTCC TGG - SEQ ID NO: 1 | CTGGCGCTTTCCTTAC CTGA - SEQ ID NO: 2 |
| TRPV1 | rs222747 | NC_000017.11:g.3589906 C > A | 3493200 | CTAAGGGGAGGTTTGGG CAG - SEQ ID NO: 3 | AGCCCTACAGGCTGGT ATGA - SEQ ID NO: 4 |
| TRPV1 | rs8065080 | NC_000017.11:g.3577153 T > C | 3480447 | GTCATGTGAGATGGGC CAA - SEQ ID NO: 5 | CAGTGTGTCCTCTGTC CACC - SEQ ID NO: 6 |
| HTR2A | rs6311 | NC_000013.11:g.46897343 C > T | 47471478 | AGGTACAGACTTGGCCA CAA - SEQ ID NO: 7 | GGCCTTTTGTGCAGAT TCCC - SEQ ID NO: 8 |

TABLE 5-continued

Primers designed for selected SNPs for testing

| Genes | SNPs | Notes | Chromosome Position | Forward Primer | Reverse Primer |
|---|---|---|---|---|---|
| HTR2A | rs6313 | NC_000013.11:g.46895805 G > A | 47469940 | GCATGTACACCAGCCTC AGT - SEQ ID NO: 9 | GTGGCATGCACATGCT CTTT - SEQ ID NO: 10 |
| ABCB1 | rs1045642 | NC_000007.14:g.87509329 A > G | 87138645 | TGAATGTTCAGTGGCTC CGA - SEQ ID NO: 11 | ACAGGAAGTGTGGCC AGATG - SEQ ID NO: 12 |
| ABCB1 | rs2032582 | NC_000007.14:g.87531302 A > C | 87160618 | GCAGGCTATAGGTTCCA GGC - SEQ ID NO: 13 | AGTCCAAGAACTGGCT TTGCT - SEQ ID NO: 14 |
| CNR1 | rs1049353 | NC_000006.12:g.88143916 C > T | 88853635 | CCGGAGCATGTTTCCCT CTT - SEQ ID NO: 15 | GTAGCCAAAGGTTTCC CTCCT - SEQ ID NO: 16 |
| CNR1 | rs2180619 | NC_000006.12:g.88168233 G > A | 88877952 | ACCAGGGTGTGTCAGTG TTG - SEQ ID NO: 17 | TGGGGAAGGCTCTACT CACA - SEQ ID NO: 18 |
| CNR1 | rs806368 | NC_000006.12:g.88140381 T > C | 88850100 | GCCCAACCACCAGATGA GAA - SEQ ID NO: 19 | TGCAACGATGTTACCA GCTCA - SEQ ID NO: 20 |
| CNR1 | rs806380 | NC_900006.12:g.88154934 A > G | 88864653 | TCACTGTTGCTATGGAC TCCT - SEQ ID NO: 21 | GTGCCTTGGCACTTTT CTTGA - SEQ ID NO: 22 |
| CNR2 | rs2229579 | NC_000001.11:g.23874672 G > A | 24201162 | GGCTGTGCTCCTCATCT GTT - SEQ ID NO: 23 | GGGTCCGTGTCTAGGT G - SEQ ID NO: 24 |
| CNR2 | rs35761398 | NC_000001.11:g.23875429_ 23875430delTTinsCC | 24201919 | AGGTGAGGTCATTCTTG TGCT - SEQ ID NO: 25 | AGTCACGCTGCCAATC TTCA - SEQ ID NO: 26 |
| COMT | rs4680 | NC_000022.11:g,19963748 G > A | 19951271 | CTGCTCTTTGGGAGAGG TGG - SEQ ID NO: 27 | CCACCTTGGCAGTTTA CCCA - SEQ ID NO: 28 |
| CYP2C19 | rs4244285 | NC_000010.11:g.94781859 G > A | 96541616 | TGTGCAAACTCTTTTAA CCTATGCT - SEQ ID NO: 29 | CACAAATACGCAAGC AGTCACA - SEQ ID NO: 30 |
| CYP2C9 | rs1057910 | NC_000010.11:g.94981296 A > C | 96741053 | ACCCCTGAATTGCTACA ACA - SEQ ID NO: 31 | ACCCGGTGATGGTAG AGGTT - SEQ ID NO: 32 |
| CYP2C9 | rs1799853 | NC_000010.11:g.94942290 C > T | 96702047 | GCAGTGAAGGAAGCCC TGAT - SEQ ID NO: 33 | CCCTTGGCTCTCAGCT TCAA - SEQ ID NO: 34 |
| CYP3A4 | rs55785340 | NC_000007.14:g.99768360 A > G | 99365983 | GTCTTTGGGGCCTACAG CAT - SEQ ID NO: 35 | AAGTGGATGAATTAC ATGGTGA - SEQ ID NO: 36 |
| CYP3A4 | rs67784355 | NC_000007.14:g.99762206 G > A | 99359829 | GGATTTCAGTCCCTGGG GTG - SEQ ID NO: 37 | GGGCCTTGTACCTTTC AGGG - SEQ ID NO: 38 |
| CYP3A4 | rs12721629 | NC_000007.14:g.99762177 G > A | 99359800 | GGATTTCAGTCCCTGGG GTG - SEQ ID NO: 39 | GGGCCTTGTACCTTTC AGGG - SEQ ID NO: 40 |
| CYP3A4 | rs4987161 | NC_000007.14:g.99768458 A > G | 99366081 | GAAGAGGAATCGGCTCT GGG - SEQ ID NO: 41 | TGAGAAAGAATGG ATCCAAAA - SEQ ID NO: 42 |
| FAAH | rs324420 | NC_000001.11:g.46405089 C > A | 46870761 | TCCCTAGTGAGGCAGAT GCT - SEQ ID NO: 43 | TGACCCAAGATGCAG AGCAG - SEQ ID NO: 44 |
| FAAH | rs2295633 | NC_000001.11:g.46408711 A > G | 46874383 | ACTGCAGGGTCCTGGAA GTA - SEQ ID NO: 45 | AACCCTGCCCACAAG ATAGC - SEQ ID NO: 46 |
| MGLL | rs604300 | NC_000003.12:g.127724009 A > G | 127442852 | GAAGGAAAGGGGAGTT GGGG - SEQ ID NO: 47 | CTAACCCCAGGATCT CGGA - SEQ ID NO: 48 |
| GABRA2 | rs279826 | NC_000004.12:g.46332192 A > G | 46334209 | CACATAATGGGGAGTG GGGG - SEQ ID NO: 49 | ACCAGTTCCATAGAAT CCAAGAGT - SEQ ID NO: 50 |
| GABRA2 | rs279858 | NC_000004.12:g.46312576 T > C | 46314593 | TGGAGCAGTTTGACTGA GACC - SEQ ID NO: 51 | ACAGCTAGATTGGCTG GTTGT - SEQ ID NO: 52 |
| GABRA2 | rs279871 | NC_000004.12:g.46303716 T > C | 46305733 | CAATATCATGGGACGTG AGCTG - SEQ ID NO: 53 | AAAACAATACTCCCCG CCCC - SEQ ID NO: 54 |

TABLE 5-continued

Primers designed for selected SNPs for testing

| Genes | SNPs | Notes | Chromosome Position | Forward Primer | Reverse Primer |
|---|---|---|---|---|---|
| MAPK14 | rs12199654 | NC_000006.12:g.36041718 A > G | 36009495 | ACTTCCGTTGGAATGGG ATTCA - SEQ ID NO: 55 | ACTGGGTTCACCCTAC CTGA - SEQ ID NO: 56 |
| NRG1 | rs17664708 | NC_000008.11:g.32579499 C > T | 32437017 | CAGCACTGGGAGGTGAT CTG - SEQ ID NO: 57 | TGTCATGTTGTTGGCT TGGA - SEQ ID NO: 58 |
| AKT1 | rs1130233 | NC_000014.9:g.104773557 C > T | 105239894 | GGGTGACTTGTTCCTGC TGA - SEQ ID NO: 59 | GCACAGAGAGGACAC AGCAT - SEQ ID NO: 60 |
| CNR2 | rs2501431 | NC_000001.11:g.23875153 G > A | 24201643 | TCTGATCCTGTCCTCCC ACC - SEQ ID NO: 61 | TCTTGGCCAACCTCAC ATCC - SEQ ID NO: 62 |
| HTR1A | rs6295 | NC_000005.10:g.63962738 C > G | 63258565 | GAGGTTTGCAGGCTCTG GTA - SEQ ID NO: 63 | GTGTCAGCATCCCAGA GTGG - SEQ ID NO: 64 |
| HTR2A | rs7997012 | NC_000013.11:g.46837850 A > G | 47411985 | CTTGGAGGCACAGCTCA TCA - SEQ ID NO: 65 | ACTGCCTCACTCTTGC CATC - SEQ ID NO: 66 |
| CNR1 | rs806371 | NC_000006.12:g.88146644 T > G | 88856363 | GATTGTCTCTCCCCCAA CCC - SEQ ID NO: 67 | AGCAGGTTGGTGACA CAAGT - SEQ ID NO: 68 |
| CNR1 | rs12720071 | NC_000006.12:g.88141462 T > C | 88851181 | TTGCCAGTCTTTTGTCCT GC - SEQ ID NO: 69 | AATGCATGGTCAGGG CAAGT - SEQ ID NO: 70 |
| CNR1 | rs1406977 | NC_000006.11:g.8884821 C > T | 88884821 | GCACACTTGTGTCACCA ACC - SEQ ID NO: 71 | ATGTGGGGAGAGATG CTCCT - SEQ ID NO: 72 |
| PTGS2 | rs20417 | NC_000001.11:g.186681189 C > G | 186650321 | CCTGCAAATTCTGGCCA TCG - SEQ ID NO: 73 | CACTTGGCTTCCTCTC GAGG - SEQ ID NO: 74 |
| SLC6A4 | 5-HTTLPR | AC104984 | 26096 | ATGCCAGCACCTAACCC CTAATGT - SEQ ID NO: 75 | GGACCGCAAGGTGGG CGGGA - SEQ ID NO: 76 |

TABLE 6A

NGS data report of SNPs

| SNP Index | db_xref | Gene | Chrom | Position | Coverage | Trans Accession |
|---|---|---|---|---|---|---|
| 1 | rs2229579 | CNR2 | 1 | 24201162 | 3004 | NM_001841.2 |
| 2 | rs2501431 | CNR2 | 1 | 24201643 | 0 | NM_001841.2 |
| 3 | rs35761398 | CNR2 | 1 | 24201919 | 3305 | NM_001841.2 |
| 4 | rs2501432 | CNR2 | 1 | 24201920 | 3275 | NM_001841.2 |
| 5 | rs324420 | FAAH | 1 | 46870761 | 4096 | NM_001441.2 |
| 6 | rs2295633 | FAAH | 1 | 46874383 | 2303 | NM_001441.2 |
| 7 | rs20417 | PTGS2 | 1 | 186650321 | 2102 | |
| 8 | rs604300 | MGLL | 3 | 127442852 | 8670 | NM_007283.5 |
| 9 | rs279871 | GABRA2 | 4 | 46305733 | 3473 | NM_000807.2 |
| 10 | rs279858 | GABRA2 | 4 | 46314593 | 470 | NM_000807.2 |
| 11 | rs279826 | GABRA2 | 4 | 46334209 | 1021 | NM_000807.2 |
| 12 | rs6295 | HTR1A | 5 | 63258565 | 998 | |
| 13 | rs12199654 | MAPK14 | 6 | 36009495 | 1203 | NM_001315.2 |
| 14 | rs806368 | CNR1 | 6 | 88850100 | 348 | NM_001160226.1 |
| 15 | rs12720071 | CNR1 | 6 | 88851181 | 1334 | NM_001160226.1 |
| 16 | rs1049353 | CNR1 | 6 | 88853635 | 4142 | NM_001160226.1 |
| 17 | rs806371 | CNR1 | 6 | 88856363 | 9379 | NM_001160226.1 |
| 18 | rs806380 | CNR1 | 6 | 88864653 | 1116 | NM_001160226.1 |
| 19 | rs2180619 | CNR1 | 6 | 88877952 | 2302 | |
| 20 | rs1406977 | CNR1 | 6 | 88884821 | 0 | |
| 21 | rs1799971 | OPRM1 | 6 | 154360797 | 4218 | NM_001145279.1 |
| 22 | rs1045642 | ABCB1 | 7 | 87138645 | 11263 | NM_000927.4 |
| 23 | rs2032582 | ABCB1 | 7 | 87160618 | 10755 | NM_000927.4 |
| 24 | rs12721629 | CYP3A4 | 7 | 99359800 | 4954 | NM_017460.5 |
| 25 | rs67784355 | CYP3A4 | 7 | 99359829 | 4756 | NM_017460.5 |
| 26 | rs55785340 | CYP3A4 | 7 | 99365983 | 6977 | NM_017460.5 |
| 27 | rs4987161 | CYP3A4 | 7 | 99366081 | 6667 | NM_017460.5 |

TABLE 6A-continued

NGS data report of SNPs

| Index | SNP db_xref | Gene | Chrom | Position | Coverage | Trans Accession |
|---|---|---|---|---|---|---|
| 28 | rs17664708 | NRG1 | 8 | 32437017 | 1277 | NM_013956.3 |
| 29 | rs4244285 | CYP2C19 | 10 | 96541616 | 737 | NM_000769.1 |
| 30 | rs28371674 | CYP2C9 | 10 | 96702047 | 1002 | NM_000771.3 |
| 31 | rs1057910 | CYP2C9 | 10 | 96741053 | 3383 | NM_000771.3 |
| 32 | rs7997012 | HTR2A | 13 | 47411985 | 5884 | NM_000621.3 |
| 33 | rs6313 | HTR2A | 13 | 47469940 | 1982 | NM_000621.3 |
| 34 | rs6311 | HTR2A | 13 | 47471478 | 1193 | |
| 35 | rs1130233 | AKT1 | 14 | 105239894 | 2057 | NM_001014431.1 |
| 36 | rs8065080 | TRPV1 | 17 | 3480447 | 1624 | NM_018727.5 |
| 37 | rs222747 | TRPV1 | 17 | 3493200 | 1 | NM_018727.5 |
| 38 | rs4680 | COMT | 22 | 19951271 | 1537 | NM_000754.3 |

TABLE 6B

NGS data report of SNPs

| Index | Reference | Alternative | A % | C % | G % | T % | Mutation Call: Relative To CDS | CDS |
|---|---|---|---|---|---|---|---|---|
| 1 | G | A | 0.23 | 0 | 99.73 | 0.03 | | 1 |
| 2 | G | — | 0 | 0 | 0 | 0 | | 1 |
| 3 | T | C | 0.15 | 53.92 | 0.33 | 45.6 | c.189A > AG | 1 |
| 4 | T | C | 0.12 | 53.25 | 0.06 | 46.56 | c.188A > AG | 1 |
| 5 | C | K | 48.19 | 51.27 | 0.27 | 0.27 | c.385C > AC | 3 |
| 6 | A | G | 1.22 | 0 | 98.74 | 0 | c.1077+127A > G | |
| 7 | C | T | 0.05 | 99.67 | 0 | 0.29 | | |
| 8 | A | G | 0.14 | 0 | 99.86 | 0 | c.263−1443T > C | |
| 9 | T | C | 0.03 | 99.91 | 0 | 0.06 | c.704−104A > G | |
| 10 | T | C | 0 | 100 | 0 | 0 | c.396A > G | 4 |
| 11 | A | G | 0.1 | 0 | 99.8 | 0.1 | c.255+423T > C | |
| 12 | C | G | 0.1 | 48.5 | 51.3 | 0.1 | c.−1019C > CG | |
| 13 | A | G | 99.42 | 0.17 | 0.42 | 0 | | |
| 14 | T | C | 0 | 47.99 | 0 | 52.01 | c.*3475A > AG | |
| 15 | T | C | 0.22 | 52.4 | 0.22 | 47.15 | c.*2394A > AG | |
| 16 | C | T | 0.05 | 99.59 | 0 | 0.36 | | 1 |
| 17 | T | C | 0.04 | 0.33 | 0.03 | 99.59 | | |
| 18 | A | G | 0 | 0 | 100 | 0 | c.−206−7128T > C | |
| 19 | G | A | 99 | 0.35 | 0.52 | 0.13 | c.−452−2185G > A | |
| 20 | C | — | 0 | 0 | 0 | 0 | | |
| 21 | A | G | 99.36 | 0.05 | 0.55 | 0.05 | | 2 |
| 22 | A | G | 99.15 | 0.18 | 0.56 | 0.1 | | 25 |
| 23 | A | G | 99.38 | 0.07 | 0.45 | 0.1 | | 20 |
| 24 | G | T | 0.16 | 0 | 99.64 | 0.2 | | 11 |
| 25 | G | A | 0.17 | 0.02 | 99.81 | 0 | | 11 |
| 26 | A | G | 99.64 | 0.04 | 0.3 | 0.01 | | 7 |
| 27 | A | G | 99.46 | 0.04 | 0.31 | 0.18 | | 7 |
| 28 | C | A | 0.08 | 99.84 | 0 | 0.08 | | |
| 29 | G | A | 0.14 | 0 | 99.73 | 0.14 | | 5 |
| 30 | C | T | 0 | 99.6 | 0.1 | 0.3 | | 3 |
| 31 | A | G | 99.29 | 0.03 | 0.62 | 0.06 | | 7 |
| 32 | A | G | 0.05 | 0 | 99.9 | 0.05 | c.614−2211T > C | |
| 33 | G | A | 48.69 | 0 | 51.16 | 0.15 | c.102C > CT | 1 |
| 34 | C | T | 0 | 49.12 | 0 | 50.88 | c.−689−309C > CT | |
| 35 | C | T | 0.05 | 48.71 | 0.05 | 51.14 | c.726G > AG | 8 |
| 36 | T | C | 0 | 1.05 | 0.12 | 98.83 | | 11 |
| 37 | C | — | 0 | 100 | 0 | 0 | | 5 |
| 38 | G | A | 48.8 | 0 | 51.2 | 0 | c.472G > AG | 2 |

Zygosity:

Heterozygous: Index #s 1-5, 7, 12-17, 20-31, and 33-38

Homozygous: Index #s 6, 8-11, 18, 19, and 32

TABLE 7

Weighting Values for Dosage Impacts of SNP Genotypes

| Gene | Gene Group | SNP | Allele | *Cannabis* Dosage | CBD Dosage | THC Dosage | Drag Dependence THC) |
|---|---|---|---|---|---|---|---|
| OPRM1 | Transporter/Receptor | rs1799971 - Refs. 37 and 11 | A/A | 1 | 1 | 1 | 1 |
| OPRM1 | Transporter/Receptor | rs1799971 - Ref. 37 | A/G | 1 | 1 | 1 | 1 |
| OPRM1 | Transporter/Receptor | rs1799971 - Ref. 37 | G/G | 1 | 1 | 1 | 1 |
| TRPV1 | Transporter/Receptor | rs222747 - Refs. 6 and 7 | C/C | 1 | 1 | 1 | 1 |
| TRPV1 | Transporter/Receptor | rs222747 - Refs. 6 and 7 | C/G | 1 | 1 | 1 | 1 |
| TRPV1 | Transporter/Receptor | rs222747- Refs. 6 and 7 | G/G | 1 | 1 | 1 | 1 |
| TRPV1 | Transporter/Receptor | rs8065080 - Refs. 6 and 14 | T/T | 1 | 1 | 1 | 1 |
| TRPV1 | Transporter/Receptor | rs8065080 - Refs. 6 and 14 | T/C | 1 | 1 | 1 | 1 |
| TRPV1 | Transporter/Receptor | rs8065080 - Refs. 6 and 14 | C/C | 1 | 0.5 | 1 | 1 |
| HTR2A | Transporter/Receptor | rs6311 - Refs. 13 and 21 | C/C | 1 | 1 | 1 | 1 |
| HTR2A | Transporter/Receptor | rs6311 - Refs. 13 and 21 | C/T | 1 | 1 | 1.5 | 1 |
| HTR2A | Transporter/Receptor | rs6311 - Refs. 13 and 21 | T/T | 1 | 1 | 1.5 | 1 |
| HTR2A | Transporter/Receptor | rs6313 - Refs. 21 and 12 | G/G | 1 | 1 | 1 | 1 |
| HTR2A | Transporter/Receptor | rs6313 - Refs. 21 and 12 | G/A | 1 | 1 | 1 | 1 |
| HTR2A | Transporter/Receptor | rs6313 - Refs. 21 and 12 | A/A | 1 | 1 | 0.64 | 1 |
| ABCB1 | Transporter/Receptor | rs1045642 - Refs. 17, 26, and 4 | A/A | 1 | 1 | 1 | 1 |
| ABCB1 | Transporter/Receptor | rs1045642 - Refs. 17, 26, and 4 | A/G | 1 | 1 | 1 | 1 |
| ABCB1 | Transporter/Receptor | rs1045642 - Refs. 17, 26, and 4 | G/G | 1 | 1 | 1 | 0.5 |
| ABCB1 | Transporter/Receptor | rs2032582 - Refs. 13 and 43 | A/A | 1 | 1 | 1 | 1 |
| ABCB1 | Transporter/Receptor | rs2032582 - Refs. 13 and 43 | A/C | 1 | 1 | 1 | 1 |
| ABCB1 | Transporter/Receptor | rs2032582 - Refs. 13 and 43 | C/C | 1 | 1 | 1 | 1 |
| CNR1 | Transporter/Receptor | rs1049353 - Refs. 24, 45, and 35 | C/C | 1.25 | 1 | 1 | 1 |
| CNR1 | Transporter/Receptor | rs1049353 - Refs. 24, 45, and 35 | C/T | 1 | 1 | 1 | 1 |
| CNR1 | Transporter/Receptor | rs1049353 - Refs. 24, 45, and 35 | T/T | 0.75 | 1 | 1 | 1 |
| CNR1 | Transporter/Receptor | rs2180619 - Refs. 46, 30, and 23 | G/G | 1 | 1 | 1 | 0.5 |
| CNR1 | Transporter/Receptor | rs2180619 - Refs. 46, 30, and 23 | G/A | 1 | 1 | 1 | 1 |
| CNR1 | Transporter/Receptor | rs2180619 - Refs. 46, 30, and 23 | A/A | 1 | 1 | 1 | 1 |
| CNR1 | Transporter/Receptor | rs806368 - Ref. 35 | T/T | 1.5 | 1 | 1 | 1 |
| CNR1 | Transporter/Receptor | rs806368 - Ref. 35 | T/C | 1 | 1 | 1 | 1 |
| CNR1 | Transporter/Receptor | rs806368 - Ref. 35 | C/C | 1 | 1 | 1 | 1 |
| CNR1 | Transporter/Receptor | rs806371 - Refs. 45 and 35 | T/T | 1 | 1 | 1 | 1 |
| CNR1 | Transporter/Receptor | rs806371 - Refs. 45 and 35 | T/G | 1 | 1 | 1 | 1 |
| CNR1 | Transporter/Receptor | rs806371 - Refs. 45 and 35 | G/G | 1 | 1 | 1 | 1 |
| CNR1 | Transporter/Receptor | rs806368-rs806371 - Ref. 45 | T/T/T/T | 1.5 | 1 | 1 | 1 |
| CNR1 | Transporter/Receptor | rs806368-rs806371 - Ref. 45 | Other | 1 | 1 | 1 | 1 |
| CNR1 | Transporter/Receptor | rs806380 - Ref. 22 | A/A | 1 | 1 | 1 | 0.75 |
| CNR1 | Transporter/Receptor | rs806380 - Ref. 22 | A/G | 1 | 1 | 1 | 1 |
| CNR1 | Transporter/Receptor | rs806380 - Ref. 22 | G/G | 1 | 1 | 1 | 1 |
| CNR1 | Transporter/Receptor | rs12720071 - Ref. 20 | T/T | 1 | 1 | 1 | 1 |
| CNR1 | Transporter/Receptor | rs12720071 - Ref. 20 | T/C | 1 | 1 | 1 | 1 |
| CNR1 | Transporter/Receptor | rs12720071 - Ref. 20 | C/C | 1 | 1 | 1 | 1 |
| CNR2 | Transporter/Receptor | rs2229579 - Refs. 44 and 9 | G/G | 1 | 1 | 1 | 1 |
| CNR2 | Transporter/Receptor | rs2229579 - Refs. 44 and 9 | G/A | 1 | 1 | 1 | 1 |
| CNR2 | Transporter/Receptor | rs2229579 - Refs. 44 and 9 | A/A | 1 | 1 | 1 | 1 |
| CNR2 | Transporter/Receptor | rs35761398 - Refs. 25 and 9 | T/T | 1 | 1 | 1 | 1 |
| CNR2 | Transporter/Receptor | rs35761398 - Refs. 25 and 9 | T/C | 1 | 1 | 1 | 1 |
| CNR2 | Transporter/Receptor | rs35761398 - Refs. 25 and 9 | C/C | 1.5 | 1 | 1 | 1 |
| CNR2 | Transporter/Receptor | rs2501432 - Refs. 25 and 9 | T/T | 1 | 1 | 1 | 1 |
| CNR2 | Transporter/Receptor | rs2501432 - Refs. 25 and 9 | T/C | 1 | 1 | 1 | 1 |
| CNR2 | Transporter/Receptor | rs2501432 - Refs. 25 and 9 | C/C | 1.5 | 1 | 1 | 1 |
| COMT | Metabolic Enzyme | rs4680 - Ref. 24 | G/G | 1 | 1 | 1 | 0.75 |
| COMT | Metabolic Enzyme | rs4680 - Ref. 24 | G/A | 1 | 1 | 1 | 1 |
| COMT | Metabolic Enzyme | rs4680 - Ref. 24 | A/A | 1 | 1 | 1 | 1 |
| CYP2C19 | Metabolic Enzyme | rs4244285 - Refs. 15 and 41 | G/G | 1 | 1 | 1 | 1 |
| CYP2C19 | Metabolic Enzyme | rs4244285 - Refs. 15 and 41 | G/A | 1 | 0.75 | 1 | 1 |
| CYP2C19 | Metabolic Enzyme | rs4244285 - Refs. 15 and 41 | A/A | 1 | 0.5 | 1 | 1 |
| CYP2C9 | Metabolic Enzyme | rs1057910 - Refs. 29 and 41 | A/A | 1 | 1 | 1 | 1 |
| CYP2C9 | Metabolic Enzyme | rs1057910 - Refs. 29 and 41 | A/C | 1 | 1 | 0.65 | 1 |
| CYP2C9 | Metabolic Enzyme | rs1057910 - Refs. 29 and 41 | C/C | 1 | 1 | 0.3 | 1 |
| CYP2C9 | Metabolic Enzyme | rs28371674 - Refs. 29 and 41 | C/C | 1 | 1 | 1 | 1 |
| CYP2C9 | Metabolic Enzyme | rs28371674 - Refs. 29 and 41 | C/T | 1 | 1 | 0.8 | 1 |
| CYP2C9 | Metabolic Enzyme | rs28371674 - Refs. 29 and 41 | T/T | 1 | 1 | 0.6 | 1 |
| CYP3A4 | Metabolic Enzyme | rs55785340 - Refs. 41 | A/A | 1 | 1 | 1 | 1 |
| CYP3A4 | Metabolic Enzyme | rs55785340 - Refs. 41 | A/G | 0.75 | 1 | 1 | 1 |
| CYP3A4 | Metabolic Enzyme | rs55785340 - Refs. 41 | G/G | 0.5 | 1 | 1 | 1 |
| CYP3A4 | Metabolic Enzyme | rs67784355 - Refs. 41 | G/G | 1 | 1 | 1 | 1 |
| CYP3A4 | Metabolic Enzyme | rs67784355 - Refs. 41 | G/A | 0.75 | 1 | 1 | 1 |
| CYP3A4 | Metabolic Enzyme | rs67784355 - Refs. 41 | A/A | 0.5 | 1 | 1 | 1 |
| CYP3A4 | Metabolic Enzyme | rs12721629 - Refs. 41 | G/G | 1 | 1 | 1 | 1 |
| CYP3A4 | Metabolic Enzyme | rs12721629 - Refs. 41 | G/A | 0.75 | 1 | 1 | 1 |
| CYP3A4 | Metabolic Enzyme | rs12721629 - Refs. 41 | A/A | 0.5 | 1 | 1 | 1 |
| CYP3A4 | Metabolic Enzyme | rs4987161 - Refs. 41 | A/A | 1 | 1 | 1 | 1 |
| CYP3A4 | Metabolic Enzyme | rs4987161 - Refs. 41 | A/G | 0.75 | 1 | 1 | 1 |
| CYP3A4 | Metabolic Enzyme | rs4987161 - Refs. 41 | G/G | 0.5 | 1 | 1 | 1 |

TABLE 7-continued

Weighting Values for Dosage Impacts of SNP Genotypes

| Gene | Gene Group | SNP | Allele | Cannabis Dosage | CBD Dosage | THC Dosage | Drug Dependence THC) |
|---|---|---|---|---|---|---|---|
| FAAH | Metabolic Enzyme | rs324420 - Refs. 33 and 40 | C/C | 1 | 1 | 1 | 1 |
| FAAH | Metabolic Enzyme | rs324420 - Refs. 33 and 40 | C/A | 1 | 0.75 | 1 | 0.75 |
| FAAH | Metabolic Enzyme | rs324420 - Refs. 33 and 40 | A/A | 1 | 0.5 | 1 | 0.5 |
| FAAH | Metabolic Enzyme | rs2295633 - Refs. 28 and 32 | A/A | 1 | 1 | 1 | 1 |
| FAAH | Metabolic Enzyme | rs2295633 - Refs. 28 and 32 | A/G | 1 | 1 | 1 | 1 |
| FAAH | Metabolic Enzyme | rs2295633 - Refs. 28 and 32 | G/G | 1 | 1 | 1 | 1 |
| MGLL | Metabolic Enzyme | rs604300 - Ref. 8 | A/A | 1 | 1 | 1 | 1 |
| MGLL | Metabolic Enzyme | rs604300 - Ref. 8 | A/G | 1 | 1 | 1 | 1 |
| MGLL | Metabolic Enzyme | rs604300 - Ref. 8 | G/G | 1 | 1 | 1 | 0.5 |
| GABRA2 | Transporter/Receptor | rs279826 - Ref. 1 | A/A | 1 | 1 | 1 | 1 |
| GABRA2 | Transporter/Receptor | rs279826 - Ref. 1 | A/G | 1 | 1 | 1 | 1 |
| GABRA2 | Transporter/Receptor | rs279826 - Ref. 1 | G/G | 1 | 1 | 1 | 1 |
| GABRA2 | Transporter/Receptor | rs279858 - Ref. 1 | T/T | 1 | 1 | 1 | 1 |
| GABRA2 | Transporter/Receptor | rs279858 - Ref. 1 | T/C | 1 | 1 | 1 | 1 |
| GABRA2 | Transporter/Receptor | rs279858 - Ref. 1 | C/C | 1 | 1 | 1 | 1 |
| GABRA2 | Transporter/Receptor | rs279871 - Ref. 1 | T/T | 1 | 1 | 1 | 1 |
| GABRA2 | Transporter/Receptor | rs279871 - Ref. 1 | T/C | 1 | 1 | 1 | 1 |
| GABRA2 | Transporter/Receptor | rs279871 - Ref. 1 | C/C | 1 | 1 | 1 | 1 |
| GABRA2 | Transporter/Receptor | rs279826-rs279858-rs279871 - Ref. 1 | A/T/T | 1 | 1 | 1 | 0.5 |
| GABRA2 | Transporter/Receptor | rs279826-rs279858-rs279871 - Ref. 1 | G/C/C | 1 | 1 | 1 | 0.75 |
| GABRA2 | Transporter/Receptor | rs279826-rs279858-rs279871 - Ref. 1 | Other | 1 | 1 | 1 | 1 |
| MAPK14 | Signaling | rs12199654 - Ref. 36 | A/A | 1 | 1 | 1 | 1 |
| MAPK14 | Signaling | rs12199654 - Ref. 36 | A/G | 1 | 1 | 1 | 1 |
| MAPK14 | Signaling | rs12199654 - Ref. 36 | G/G | 1 | 1 | 1 | 1 |
| MAPK14/CNR1 | Signaling | rs12199654-rs12720071 - Ref. 36 | A/A/T/C | 1 | 1 | 1 | 0.5 |
| MAPK14/CNR1 | Signaling | rs12199654-rs12720071 - Ref. 36 | A/A/C/C | 1 | 1 | 1 | 0.5 |
| NRG1 | Signaling | rs17664708 - Ref. 19 | C/C | 1 | 1 | 1 | 1 |
| NRG1 | Signaling | rs17664708 - Ref. 19 | C/T | 1 | 1 | 1 | 0.75 |
| NRG1 | Signaling | rs17664708 - Ref. 19 | T/T | 1 | 1 | 1 | 0.5 |
| AKT1 | Signaling | rs1130233 - Ref. 5 | C/C | 1 | 1 | 1 | 1 |
| AKT1 | Signaling | rs1130233 - Ref. 5 | C/T | 1 | 1 | 0.5 | 1 |
| AKT1 | Signaling | rs1130233 - Ref. 5 | T/T | 1 | 1 | 0.5 | 1 |
| CNR2 | Transporter/Receptor | rs2501431 - Ref. 24 | | 1 | 1 | 1 | 1 |
| CNR2 | Transporter/Receptor | rs2501431 - Ref. 24 | | 1 | 1 | 1 | 1 |
| CNR2 | Transporter/Receptor | rs2501431 - Ref. 24 | | 1 | 1 | 1 | 1 |
| HTR1A | Transporter/Receptor | rs6295 - Refs. 2 and 3 | C/C | 1 | 1 | 1 | 1 |
| HTR1A | Transporter/Receptor | rs6295 - Refs. 2 and 3 | C/G | 1.5 | 1 | 1 | 1 |
| HTR1A | Transporter/Receptor | rs6295 - Refs. 2 and 3 | G/G | 1.5 | 1 | 1 | 1 |
| HTR2A | Transporter/Receptor | rs7997012 - Ref. 34 | A/A | 1 | 1 | 1 | 1 |
| HTR2A | Transporter/Receptor | rs7997012 - Ref. 34 | A/G | 1 | 1 | 1 | 1 |
| HTR2A | Transporter/Receptor | rs7997012 - Ref. 34 | G/G | 1 | 1 | 1.22 | 1 |
| CNR1 | Transporter/Receptor | rs1406977 - Ref. 24 | | 1 | 1 | 1 | 1 |
| CNR1 | Transporter/Receptor | rs1406977 - Ref. 24 | | 1 | 1 | 1 | 1 |
| CNR1 | Transporter/Receptor | rs1406977 - Ref. 24 | | 1 | 1 | 1 | 1 |
| PTGS2 | Metabolic Enzyme | rs20417 - Refs. 16, 10, and 24 | C/C | 1 | 1 | 1 | 1 |
| PTGS2 | Metabolic Enzyme | rs20417 - Refs. 16, 10, and 24 | C/G | 1 | 1 | 1 | 1 |
| PTGS2 | Metabolic Enzyme | rs20417 - Refs. 16, 10, and 24 | G/G | 1 | 1 | 1 | 1 |
| SLC6A4 | Transporter/Receptor | 5-HTTLPR - Ref. 24 | | 1 | 1 | 1 | 1 |
| SLC6A4 | Transporter/Receptor | 5-HTTLPR - Ref. 24 | | 1 | 1 | 1 | 1 |
| SLC6A4 | Transporter/Receptor | 5-HTTLPR - Ref. 24 | | 1 | 1 | 1 | 1 |

TABLE 8

Weighting Values for Genotypes of a Test Example

| Gene | Gene Group | SNP | Allele | Cannabis Dosage ($a_i$) | CBD Dosage ($b_i$) | THC Dosage ($c_i$) | Drug Dependence (THC) ($d_i$) |
|---|---|---|---|---|---|---|---|
| OPRM1 | Transporter/Receptor | rs1799971 | A/A | 1 | 1 | 1 | 1 |
| TRPV1 | Transporter/Receptor | rs8065080 | T/T | 1 | 1 | 1 | 1 |
| HTR2A | Transporter/Receptor | rs6311 | C/T | 1 | 1 | 1.5 | 1 |
| HTR2A | Transporter/Receptor | rs6313 | G/A | 1 | 1 | 1 | 1 |
| ABCB1 | Transporter/Receptor | rs1045642 | A/A | 1 | 1 | 1 | 1 |

TABLE 8-continued

Weighting Values for Genotypes of a Test Example

| Gene | Gene Group | SNP | Allele | Cannabis Dosage ($a_i$) | CBD Dosage ($b_i$) | THC Dosage ($c_i$) | Drug Dependence (THC) ($d_i$) |
|---|---|---|---|---|---|---|---|
| ABCB1 | Transporter/Receptor | rs2032582 | A/A | 1 | 1 | 1 | 1 |
| CNR1 | Transporter/Receptor | rs1049353 | C/C | 1.25 | 1 | 1 | 1 |
| CNR1 | Transporter/Receptor | rs2180619 | A/A | 1 | 1 | 1 | 1 |
| CNR1 | Transporter/Receptor | rs806368 | T/C | 1 | 1 | 1 | 1 |
| CNR1 | Transporter/Receptor | rs806371 | T/T | 1 | 1 | 1 | 1 |
| CNR1 | Transporter/Receptor | rs806380 | G/G | 1 | 1 | 1 | 1 |
| CNR1 | Transporter/Receptor | rs12720071 | T/C | 1 | 1 | 1 | 1 |
| CNR2 | Transporter/Receptor | rs2229579 | G/G | 1 | 1 | 1 | 1 |
| CNR2 | Transporter/Receptor | rs35761398 | T/C | 1 | 1 | 1 | 1 |
| CNR2 | Transporter/Receptor | rs2501432 | T/C | 1 | 1 | 1 | 1 |
| COMT | Metabolic Enzyme | rs4680 | G/A | 1 | 1 | 1 | 1 |
| CYP2C19 | Metabolic Enzyme | rs4244285 | G/G | 1 | 1 | 1 | 1 |
| CYP2C9 | Metabolic Enzyme | rs1057910 | A/A | 1 | 1 | 1 | 1 |
| CYP2C9 | Metabolic Enzyme | rs28371674 | C/C | 1 | 1 | 1 | 1 |
| CYP3A4 | Metabolic Enzyme | rs55785340 | A/A | 1 | 1 | 1 | 1 |
| CYP3A4 | Metabolic Enzyme | rs67784355 | G/G | 1 | 1 | 1 | 1 |
| CYP3A4 | Metabolic Enzyme | rs12721629 | G/G | 1 | 1 | 1 | 1 |
| CYP3A4 | Metabolic Enzyme | rs4987161 | A/A | 1 | 1 | 1 | 1 |
| FAAH | Metabolic Enzyme | rs324420 | C/A | 1 | 0.75 | 1 | 0.75 |
| FAAH | Metabolic Enzyme | rs2295633 | G/G | 1 | 1 | 1 | 1 |
| MGLL | Metabolic Enzyme | rs604300 | G/G | 1 | 1 | 1 | 0.5 |
| GABRA2 | Transporter/Receptor | rs279826 | G/G | 1 | 1 | 1 | 1 |
| GABRA2 | Transporter/Receptor | rs279858 | C/C | 1 | 1 | 1 | 1 |
| GABRA2 | Transporter/Receptor | rs279871 | C/C | 1 | 1 | 1 | 1 |
| GABRA2 | Transporter/Receptor | rs279826-rs279858-rs279871 | G/C/C | 1 | 1 | 1 | 0.75 |
| MAPK14 | Signaling | rs12199654 | A/A | 1 | 1 | 1 | 1 |
| MAPK14/CNR1 | Signaling | rs12199654-rs12720071 | A/A/T/C | 1 | 1 | 1 | 0.5 |
| NRG1 | Signaling | rs17664708 | C/C | 1 | 1 | 1 | 1 |
| AKT1 | Signaling | rs1130233 | C/T | 1 | 1 | 0.5 | 1 |
| HTR1A | Transporter/Receptor | rs6295 | C/G | 1.5 | 1 | 1 | 1 |
| HTR2A | Transporter/Receptor | rs7997012 | G/G | 1 | 1 | 1.22 | 1 |
| PTGS2 | Metabolic Enzyme | rs20417 | C/C | 1 | 1 | 1 | 1 |

TABLE 9

Calculated dosage and ratio for examples (see FIG. 4 and associated text)

| Conditions | Dosage (mg) | Body Weight (lb) | Body Weight Adjustment (D1) | CBD/THC Standard Ratio (R1) | Genetic Test Adjusted CBD (C3) | Genetic Test Adjusted THC (T3) | *Cannabis* Dependence Adjusted CBD (C4) | *Cannabis* Dependence Adjusted THC (T4) | Final Ratio ($R_f$) | Final Dosage ($D_f$) |
|---|---|---|---|---|---|---|---|---|---|---|
| Insomnia | 0.5-20 | 181-190 | 9.5 | 16:1 | 12.6 | 1.0 | 13.4 | 0.1 | 99 | 13.5 |
| Anxiety/Depression | 10-100 | 181-190 | 57 | 20:1 | 76.3 | 4.7 | 80.3 | 0.7 | 123 | 81.0 |
| Pain | 10-100 | 181-190 | 57 | 4:1 | 64.1 | 19.6 | 80.9 | 2.8 | 29 | 83.7 |

TABLE 10

Variants showing statistically significant association with pain.

| | rs2501432(Genotype): | | | | rs6311(Genotype): | | |
|---|---|---|---|---|---|---|---|
| Group | C/C(freq) | C/T(freq) | T/T(freq) | Group | C/C(freq) | C/T(freq) | T/T(freq) |
| Pain | 4(0.333) | 8(0.667) | 0(0.000) | Pain | 5(0.455) | 6(0.545) | 0(0.000) |
| No pain | 1(0.333) | 0(0.000) | 2(0.667) | No pain | 1(0.333) | 0(0.000) | 2(0.667) |
| | Fisher's p value is 0.006772 | | | | Fisher's p value is 0.010876 | | |
| | Pearson's p value is 0.006738 | | | | Pearson's p value is 0.010832 | | |

TABLE 11

Genetic variants and their functions and impact on CBD/THC dosage identified from saliva samples 1002 and 1013.

| Sample ID | Genes | Gene Family | SNPs | Alleles | Brief Functional Description |
|---|---|---|---|---|---|
| 1002 | CNR1 | Transporter and Receptor Genes | rs806371 | T/G | CNR1 Variant: Associated with a reduced response to drug-based treatments for depression and less responsive to THC. |
| 1002 | GA8RA2 | Transporter and Receptor Genes | rs279826-rs279858-rs279871 | G/C/C | GABRA2 Variant: Associated with increased risk of alcohol and THC dependence. |
| 1002 | COMT | Metabolic Enzyme Genes | rs4680 | G/G | COMT Variant: Associated with increased risk of exhibiting THC-induced cognitive impairment that may result in sleep disorders and/or anxiety. |
| 1002 | CYP2C9 | Metabolic Enzyme Genes | rs28371674 | T/T | CYP2C9 Variant: Associated with a decrease in metabolizing certain drugs and THC, leading to an increase persistence of THC in the body. |
| 1002 | FAAH | Metabolic Enzyme Genes | rs324420 | C/A | FAAH Variant: Associated with increased risk for substance use disorders. |
| 1002 | PTGS2 | Metabolic Enzyme Genes | rs20417 | G/G | PTGS2 Variant: May lead to enhanced neuropsychiatric and cognitive side effects of THC exposure |
| 1013 | HTR2A | Transporter and Receptor Genes | rs6311 | C/T | HTR2A Variant: Less responsive to anti-depressants and THC. |
| 1013 | CNR1 | Transporter and Receptor Genes | rs806368 | T/T | CNR1 Variant: Associated with response to drug-based treatments for depression, |
| 1013 | CNR1 | Transporter and Receptor Genes | rs806368-rs806371 | T/T/T/T | CNR1 Variant: Associated with the risk of the reduced efficacy in antidepressant and cannabis treatment(s). |
| 1013 | CNR2 | Transporter and Receptor Genes | rs35761398 | C/C | CNR2 Variant: Reduced receptor activity and may increase the risk of depression and alcohol dependence. |
| 1013 | CNR2 | Transporter and Receptor Genes | rs2501432 | C/C | CNR2 Variant: Reduced receptor activity and may increase the risk of depression and alcohol dependence. |
| 1013 | NRG1 | Signaling Genes | rs17664708 | C/T | NRG1 Variant: Associated with certain levels of substance dependence. |
| 1013 | AKT1 | Signaling Genes | rs1130233 | C/T | AKT1 Variant: Associated with lower tolerances to THC. |
| 1013 | CYP2C9 | Metabolic Enzyme Genes | rs1057910 | A/C | CYP2C9 Variant: Associated with a decrease in metabolizing certain drugs and THC, leading to an increase persistence of THC in the body. |
| 1013 | MGLL | Metabolic Enzyme Genes | rs604300 | G/G | MGLL Variant: Associated with increased risk for substance use disorders. |

TABLE 12

Number of CBD/THC dosage relevant variants identified from different participant samples.

| Saliva Sample ID | Metabolic Enzyme Genes | Signaling Genes | Transporter and Receptor Genes | Grand Total |
|---|---|---|---|---|
| 1002 | 4 | | 2 | 6 |
| 1003 | 3 | | 6 | 9 |
| 1004 | 3 | | 3 | 6 |
| 1005 | 2 | 1 | 4 | 7 |
| 1006 | 3 | 1 | 6 | 10 |
| 1007 | 2 | 1 | 3 | 6 |
| 1008 | 4 | 1 | 6 | 11 |
| 1012 | 3 | | 9 | 12 |
| 1013 | 2 | 2 | 5 | 9 |
| 1014 | 1 | | 4 | 5 |
| 1015 | 3 | 1 | 3 | 7 |
| 1016 | 3 | 1 | 7 | 11 |
| 1017 | 2 | 1 | 6 | 9 |
| 1018 | 3 | 2 | 7 | 12 |
| 1019 | 3 | 1 | 11 | 15 |
| 1020 | 3 | | 5 | 8 |
| 1021 | 2 | 1 | 4 | 7 |
| 1022 | 3 | 1 | 4 | 8 |
| 1023 | 2 | 2 | 5 | 9 |

What is claimed as new and desired to be protected by Letters Patent is:

1. A method of providing a personalized cannabinoid treatment regimen to a patient, the method comprising:
    obtaining two or more base values comprising:
        a base dosage for a combination of a first cannabinoid and a second cannabinoid; and
        a base ratio of the first and second cannabinoids;
    for each of a plurality of single nucleotide polymorphisms (SNPs) in a selected set of SNPs, obtaining, from a genetic test of the patient, a genotype for the SNP;
    for each of the SNPs in the selected set of SNPs, obtaining, for the obtained genotype of the SNP, at least one weighting value which reflects, for the obtained genotype of the SNP, one or more responses selected from the following: i) a response to the first and second cannabinoids; ii) a response to the first cannabinoid only; iii) a response to the second cannabinoid only; or iv) cannabinoid dependency;
    modifying the two or more base values based on the obtained weighting values to produce two or more regimen values, wherein each of the regimen values is a different one of the following: a) a regimen dosage for the first cannabinoid; b) a regimen dosage for the second cannabinoid; c) a regimen dosage for a combination of the first and second cannabinoids; or d) a regimen ratio of the first and second cannabinoids,
    wherein the modifying comprises multiplying the base dosage for the combination of the first and second cannabinoids by a product of a one of the weighting values, reflecting the response to the first and second cannabinoids, for each of a plurality of the SNPs to obtain a first intermediate value, and multiplying the first intermediate value by the base ratio of the first and second cannabinoids and dividing by 1+the base ratio of the first and second cannabinoids to produce a second intermediate value; and
    treating the patient using the first and second cannabinoids according to the two or more regimen values.

2. The method of claim 1, wherein the first cannabinoid is cannabidiol (CBD) and the second cannabinoid is $\Delta^9$-tetrahydrocannabinol (THC).

3. The method of claim 1, further comprising obtaining a condition for treatment, wherein the selected set of SNPs comprises a plurality of SNPs associated with the condition.

4. The method of claim 3, wherein a value of at least one of the base values is dependent on the condition.

5. The method of claim 3, wherein the condition is selected from pain, depression, anxiety, fear, sleep disorder, insomnia, energy metabolism disorder, inflammation, neuroprotection, Alzheimer's disease, Huntington's disease, Parkinson's disease, emesis, gastrointestinal disorder, cardiovascular disorder, cancer, nausea, vomiting, epilepsy, psychosis, diseases of the basal ganglia, neurodegenerative diseases, autoimmune disorder, retinal diseases, arthritis, convulsions, neoplastic diseases, or any combination thereof.

6. The method of claim 3, wherein the selected set of SNPs further comprises a plurality of SNPs associated with response to at least one of the first or second cannabinoids.

7. The method of claim 6, wherein the selected set of SNPs further comprises a plurality of SNPs associated with cannabinoid dependency.

8. The method of claim 1, wherein modifying the two or more base values comprises modifying at least one of the base values by multiplying the at least one of the base values by a product of at least one of the weighting values for each of a plurality of the SNPs.

9. The method of claim 1, wherein obtaining at least one weighting value comprises obtaining the weighting values for each of the following responses individually:
    i) the response to the first and second cannabinoids, ii) the response to the first cannabinoid only;
    iii) the response to the second cannabinoid only, and iv) the cannabinoid dependency.

10. The method of claim 9, wherein modifying the two or more base values comprises modifying at least one first value, selected from the two or more base values, using the weighting values for a first one of the responses to produce at least one first intermediate value; modifying at least one second value, selected from the two or more base values and the at least one first intermediate value, using the weighting values for a second one of the responses to produce at least one second intermediate value;

modifying at least one third value, selected from the two or more base values, the at least one first intermediate value, or the at least one second intermediate value, using the weighting values for a third one of the responses to produce at least one third intermediate value;

and modifying at least one fourth value, selected from the two or more base values, the at least one first intermediate value, the at least one second intermediate value, and the at least one third intermediate value, using the weighting values for a fourth one of the responses to produce at least one of the regimen values.

11. The method of claim 1, wherein obtaining the two or more base values comprises determining the two or more base values using at least one factor selected from patient weight, condition for treatment, patient age, patient gender, patient body type, other medications taken by patient, or results of a patient blood test.

12. The method of claim 1, wherein the modifying further comprises dividing the first intermediate value by 1+the base ratio of the first and second cannabinoids to produce a third intermediate value.

13. The method of claim 12, wherein the modifying further comprises multiplying the second intermediate value by a product of a one of the weighting values, reflecting the response to the first cannabinoid, for each of a plurality of the SNPs to obtain a fourth intermediate value.

14. The method of claim 13, wherein the modifying further comprises multiplying the third intermediate value by a product of a one of the weighting values, reflecting the response to the second cannabinoid, for each of a plurality of the SNPs to obtain a fifth intermediate value.

15. The method of claim 14, wherein the modifying further comprises multiplying the third intermediate value by a product of a one of the weighting values, reflecting cannabinoid dependency, for each of a plurality of the SNPs to obtain the regimen dosage for the second cannabinoid.

16. The method of claim 15, wherein the modifying further comprises producing a regimen dosage for the first cannabinoid by adding the fourth intermediate value and the fifth intermediate value and subtracting the regimen dosage for the second cannabinoid.

* * * * *

SEQUENCE LISTING

<160> NUMBER OF SEQ ID NOS: 76

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aaaagtctcg gtgctcctgg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggcgcttt ccttacctga                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctaaggggag gtttgggcag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccctacag gctggtatga                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtcatgtgag atggggccaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtgtgtcc tctgtccacc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggtacagac ttggccacaa                                              20

<210> SEQ ID NO 8

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccttttgt gcagattccc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcatgtacac cagcctcagt                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtggcatgca catgctcttt                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaatgttca gtggctccga                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acaggaagtg tggccagatg                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaggctata ggttccaggc                                                    20

<210> SEQ ID NO 14
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agtccaagaa ctggctttgc t                                              21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccggagcatg tttccctctt                                                20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtagccaaag gtttccctcc t                                              21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
accagggtgt gtcagtgttg                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggggaaggc tctactcaca                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccaaccac cagatgagaa                                                20

<210> SEQ ID NO 20
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 20
tgcaacgatg ttaccagctc a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcactgttgc tatggactcc t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgccttggc acttttcttg a                                              21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggctgtgctc ctcatctgtt                                                20

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtccgtgt ctaggtg                                                   17

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aggtgaggtc attcttgtgc t                                              21

<210> SEQ ID NO 26
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
agtcacgctg ccaatcttca                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgctctttg ggagaggtgg                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccaccttggc agtttaccca                                                    20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgtgcaaact cttttaacct atgct                                              25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacaaatacg caagcagtca ca                                                 22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acccctgaat tgctacaaca                                                    20

<210> SEQ ID NO 32
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 32
acccggtgat ggtagaggtt                                             20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcagtgaagg aagccctgat                                             20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cccttggctc tcagcttcaa                                             20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtctttgggg cctacagcat                                             20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aagtggatga attacatggt ga                                          22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggatttcagt ccctggggtg                                             20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gggccttgta cctttcaggg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggatttcagt ccctggggtg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggccttgta cctttcaggg                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaagaggaat cggctctggg                                              20

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgagagaaag aatggatcca aaa                                          23

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tccctagtga ggcagatgct                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgacccaaga tgcagagcag                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
actgcagggt cctggaagta                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaccctgccc acaagatagc                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaaggaaagg ggagttgggg                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctaaccccca ggatctcgga                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cacataatgg ggagtggggg                                              20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
accagttcca tagaatccaa gagt                                          24

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tggagcagtt tgactgagac c                                             21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acagctagat tggctggttg t                                             21

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caatatcatg ggacgtgagc tg                                            22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaaacaatac tccccgcccc                                               20

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acttccgttg gaatgggatt ca                                            22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```
actgggttca ccctacctga                                           20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagcactggg aggtgatctg                                           20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgtcatgttg ttggcttgga                                           20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gggtgacttg ttcctgctga                                           20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcacagagag gacacagcat                                           20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tctgatcctg tcctcccacc                                           20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

```
tcttggccaa cctcacatcc                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaggtttgca ggctctggta                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtgtcagcat cccagagtgg                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cttggaggca cagctcatca                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
actgcctcac tcttgccatc                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gattgtctct cccccaaccc                                                    20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agcaggttgg tgacacaagt                                                    20
```

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttgccagtct tttgtcctgc                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aatgcatggt cagggcaagt                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcacacttgt gtcaccaacc                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atgtggggag agatgctcct                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cctgcaaatt ctggccatcg                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cacttggctt cctctccagg                                              20

```
<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atgccagcac ctaaccccta atgt                                            24

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggaccgcaag gtgggcggga                                                 20
```